(12) United States Patent
Coveney

(10) Patent No.: US 12,144,545 B2
(45) Date of Patent: Nov. 19, 2024

(54) EYE TEST

(71) Applicant: SPEQS Limited, Dalkeith (AU)

(72) Inventor: David Stuart Coveney, Dalkeith (AU)

(73) Assignee: SPEQS LIMITED, North Perth (AU)

( * ) Notice: Subject to any disclaimer, the term of this patent is extended or adjusted under 35 U.S.C. 154(b) by 594 days.

(21) Appl. No.: 17/596,264

(22) PCT Filed: May 29, 2020

(86) PCT No.: PCT/AU2020/050552
§ 371 (c)(1),
(2) Date: Dec. 6, 2021

(87) PCT Pub. No.: WO2020/243771
PCT Pub. Date: Dec. 10, 2020

(65) Prior Publication Data
US 2022/0304572 A1    Sep. 29, 2022

(30) Foreign Application Priority Data

Jun. 7, 2019 (AU) ................................ 2019901987

(51) Int. Cl.
*A61B 3/032* (2006.01)
*A61B 3/00* (2006.01)
(Continued)

(52) U.S. Cl.
CPC .......... *A61B 3/0325* (2013.01); *A61B 3/0025* (2013.01); *A61B 3/0033* (2013.01);
(Continued)

(58) Field of Classification Search
CPC ... A61B 3/0325; A61B 3/0025; A61B 3/0033; A61B 3/0041; A61B 3/12; A61B 3/18
(Continued)

(56) References Cited

U.S. PATENT DOCUMENTS

2015/0219924 A1 * 8/2015 Moine .................... G02C 7/028
351/159.42

FOREIGN PATENT DOCUMENTS

WO    WO-2008049503 A2 *  5/2008 ........... A61B 3/1015

* cited by examiner

*Primary Examiner* — James R Greece
(74) *Attorney, Agent, or Firm* — Gottlieb, Rackman & Reisman, PC

(57) ABSTRACT

A system and method for an eye test application for mobile devices and in particular to applications for self-determination of eyeglass prescription via mobile computing devices comprising Simultaneous Split Point Focus (SSPF) and Low Latency Dynamic Distance Monitoring (LLDDM) for enabling self-determination of eyeglass prescription for a user via a mobile computing device, the device comprising: volatile and non-volatile memory for storing data; a processor configured for executing program instructions stored in the non-volatile memory; a visual display screen adapted to receive image information from the processor to present instructions and images to a user; and a camera configured to receive images of the user's pupils during a test situation; wherein the system comprises application program instructions for directing the processor to undertake a method for determining an eyeglass prescription, the method comprising: determining if an eye of the user is myopic, and if the user's eye is myopic; determining Principal and Axis Meridians of a user's eyes while the user is observing the image information on the display screen; enabling the system of LLDDM for real time determination of the refractive power errors in the Principal and Axis Meridians of a user's eyes in while the user is observing the SSPF image information on the display screen; calculating Sphere, Cylinder and Axis prescriptions from the Principal and Axis Meridian values obtained via the LLDDM system; and displaying the calculated prescription values to the user.

18 Claims, 11 Drawing Sheets

(51) Int. Cl.
*A61B 3/12* (2006.01)
*A61B 3/14* (2006.01)
*A61B 3/18* (2006.01)

(52) U.S. Cl.
CPC .............. *A61B 3/0041* (2013.01); *A61B 3/12* (2013.01); *A61B 3/145* (2013.01); *A61B 3/18* (2013.01)

(58) Field of Classification Search
USPC .................................................. 351/223, 246
See application file for complete search history.

EYE TEST

FIELD OF THE INVENTION

The present invention relates to eye test applications for mobile devices and in particular to applications for self-determination of eyeglass prescription via mobile computing devices and generally related to determining an eyeglass and/or a contact lens prescription for a patient with a refractive error in one or both eyes in need of correction to restore the patient's visual acuity.

The invention has been developed primarily for use in methods and systems for DIY systems and methods for self-determination of eyeglass prescription values via mobile devices and will be described hereinafter with reference to this application. However, it will be appreciated that the invention is not limited to this particular field of use.

BACKGROUND OF THE INVENTION

Any discussion of the background art throughout the specification should in no way be considered as an admission that such background art is prior art, nor that such background art is widely known or forms part of the common general knowledge in the field in Australia or worldwide.

All references, including any patents or patent applications, cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents forms part of the common general knowledge in the art, in Australia or in any other country.

Visual acuity commonly refers to the clarity of vision. Visual acuity is dependent on optical and neural factors, for example:
- the sharpness of the retinal focus within the eye;
- the health and functioning of the retina; and
- the sensitivity of the interpretative faculty of the brain.

A common cause of low visual acuity is refractive error (ametropia), or errors in how the light is refracted in the eyeball. Causes of refractive errors include aberrations in the shape of the eyeball or the cornea, and reduced flexibility of the lens. Too high or too low refractive power (in relation to the length of the eyeball) is the cause of near sightedness (myopia) or far sightedness (hyperopia) (normal refractive status is referred to as emmetropia). Other optical causes are astigmatism or more complex corneal irregularities. These anomalies can mostly be corrected by optical means (such as eyeglasses, contact lenses, laser surgery, etc.).

Spectacles (herein referred to interchangeably as spectacles, eyeglasses, contact lenses, or simply, glasses) are primarily used to improve a person's vision through external correction of any refractive error of the eyes. In order to obtain spectacles, the person must first obtain a spectacle prescription (herein referred to as a spectacle prescription, eyeglass prescription, or simply a prescription).

Many people have refractive errors of the eye which cause them to be either myopic (nearsighted) or hypermetropic (farsighted). The skilled addressee will understand that myopia refers to a refractive defect of the optical properties of an eye that causes images to focus forward of the retina (i.e. a refractive error). Those optical defects are typically caused by, among other things, defects of the cornea, elongation of the eye structure, other conditions, or a combination of those conditions. Hyperopia, on the other hand, refers a refractive error of the optical properties of an eye that causes images to focus behind the retina. Those optical defects are the result when the optics of the eye are not strong enough for the front to back length of the eye. Myopia and hyperopia have one component, a Sphere measurement, which indicates the strength or power necessary to correct for the optical defects.

Astigmatism refers to a refractive error that causes light entering the eye to focus on two points rather than one. It is caused by an uneven (optical) power of the cornea and or crystalline lens. Most commonly, the astigmatic eye's cornea has a toroidal surface. Ocular astigmatism has two components, an axis measurement (Axis), which indicates the angle along which the toroidal optics are oriented, and a Cylinder measurement, which indicates the strength or power of the toroidal optics. Myopia, hyperopia, and astigmatism are the principle refractive errors that cause patients to seek treatment to correct their vision problems.

Manifest refraction analysis is a diagnostic tool used by ophthalmologists and optometrists whereby a patient's refractive error is tested to indicate whether the patient would benefit from correction with glasses or contact lenses. As part of that technique, a patient looks through a phoropter while the ophthalmologist or optometrist evaluates each of the patient's eyes. A retinal reflex diagnosis technique is often used to assess the magnitude of the refractive error present in the patient's eyes. Subjective feedback from the patient is used to refine the manifest refraction, which involves the patient making choices between image quality as different lenses having different powers are slid into place in the phoropter. These refractive errors can be corrected with lenses, typically spectacle lenses, known as glasses, or contact lenses, which are applied directly to the eye. They can also be corrected with various types of surgery, for example Laser-Assisted In-Situ Keratomileusis (LASIK). At the end of the manifest refraction analysis, the ophthalmologist or optometrist may produce a prescription for glasses, contact lenses, and/or refractive surgery.

Other methods for determining the refractive error of a patient include known diagnostic devices such wavefront sensors, refractometers, and others that are well known in the art. Some of these diagnostic devices use computers to assist in determining the refractive error of the patient. For example, one implementation of a wavefront-type refractor that is well known in the art uses a "Hartmann-Shack" sensor to measure the wavefront of a light beam generated from an illumination spot projected on the retina and passed through the eye's optics. In such a wavefront type refractor, a probe beam from a laser or a super-luminescent diode is projected onto the retina through the eye's optics. Light scattered by the retina passes through the eye's optics and emerges through the eye's pupil. The wavefront of the emerging beam carries refractive information relating to the eye's optics. For example, if the eye is emmetropic (i.e. the eye's optics are without refractive error), the wavefront of the emerging beam should be flat. Relay optics relay the wavefront emerging from eye's pupil onto the Hartmann-Shack sensor. The Hartmann-Shack sensor measures the distortion of the wavefront and provides that information to a computer to compute the refractive errors of the eye due to aberrations of the eye's optics which may then be translated into a refractive correction prescription which is specific to the patient to correct their vision.

Each of the above-described techniques for determining a patient's refractive error requires the patient to travel to a place where such machines or doctors are present and available to perform the determination including specialist staff to operate the machines. And, having travelled to a doctor's office, a patient then has to pay for the time and services of the doctor, which may or may not be covered by their health insurance. This can be both expensive and inconvenient for a patient and provides a technical barrier for the patient to obtain a prescription using alternate and/or more accessible methods.

In addition, the cost of the above described machinery (phoropter, wavefront refractor, etc.) is prohibitive to ownership by an individual not engaged in a medical practice, so patients do not have the option of determining their own glasses or contacts prescription outside of a medical practice setting.

Therefore, there is a need fora user-operable system capable of determining the optical correction of a user for the purpose of purchasing prescription eyewear (eyeglasses/spectacles) for correction/improvement in the user's specific and individual refractive error and to overcome the technical problem of being limited to the use of highly specialised technical visual assessment equipment and operation thereof by highly specialised professionals.

SUMMARY OF THE INVENTION

It is an object of the present invention to overcome or ameliorate at least one or more of the disadvantages of the prior art, or to provide a useful alternative.

One embodiment provides a computer program product for performing a method as described herein.

One embodiment provides a non-transitive carrier medium for carrying computer executable code that, when executed on a processor, causes the processor to perform a method as described herein.

One embodiment provides a system configured for performing a method as described herein.

According to a first aspect of the invention, there is provided a system comprising Simultaneous Split Point Focus (SSPF) and Low Latency Dynamic Distance Monitoring (LLDDM) for enabling self-determination of eyeglass prescription for a user via a mobile computing device. The device may comprise volatile and non-volatile memory for storing data. The device may further comprise a processor configured for executing program instructions stored in the non-volatile memory. The device may further comprise a visual display screen adapted to receive image information from the processor to present instructions and images to a user. The device may further comprise a camera configured to receive images of the user's pupils during a test situation. The system may comprise application program instructions for directing the processor to undertake a method for determining an eyeglass prescription. The method may comprise the step of determining if an eye of the user is myopic. If the user's eye is myopic, the method may comprise the further step of determining Principal and Axis Meridians of a user's eyes while the user is observing the image information on the display screen. The method may further comprise the step of enabling the system of LLDDM for real time determination of the refractive power errors in the Principal and Axis Meridians of a user's eyes in while the user is observing the SSPF image information on the display screen. The method may comprise the step of calculating Sphere, Cylinder and Axis prescriptions from the Principal and Axis Meridian values obtained via the LLDDM system.

The method may comprise the step of displaying the calculated prescription values to the user.

According to a particular arrangement of the first aspect, there is provided a system comprising Simultaneous Split Point Focus (SSPF) and Low Latency Dynamic Distance Monitoring (LLDDM) for enabling self-determination of eyeglass prescription for a user via a mobile computing device, the device comprising:

volatile and non-volatile memory for storing data;

a processor configured for executing program instructions stored in the non-volatile memory;

a visual display screen adapted to receive image information from the processor to present instructions and images to a user; and a camera configured to receive images of the user's pupils during a test situation;

wherein the system comprises application program instructions for directing the processor to undertake a method for determining an eyeglass prescription, the method comprising:

determining if an eye of the user is myopic, and if the user's eye is myopic;

determining Principal and Axis Meridians of a user's eyes while the user is observing the image information on the display screen;

enabling the system of LLDDM for real time determination of the refractive power errors in the Principal and Axis Meridians of a user's eyes in while the user is observing the SSPF image information on the display screen;

calculating Sphere, Cylinder and Axis prescriptions from the Principal and Axis Meridian values obtained via the LLDDM system; and displaying the calculated prescription values to the user.

The determining if an eye of the user is myopic may comprise a method implemented by execution of program instructions in the processor, the method comprising:

displaying an image on the display screen comprising a first portion having a duochrome background; providing instructions to the user; and receiving input from the user with respect to a portion of the image which appears subjectively clearer to the user.

Determining the Axis Meridian may comprise a method implemented by execution of program instructions in the processor, the method comprising:

displaying a radially oriented image on the display screen; providing instructions to the user; and receiving input from the user with respect to a portion of the radially oriented image which appears subjectively clearer to the user.

Determining the Principal Meridians may comprise a method implemented by execution of program instructions in the processor, the method comprising:

displaying a hash line image on the display screen comprising a duochrome background and receiving input from the user with respect to a location spaced from the users eye under test where the lines appears subjectively equally clear to the user; and determining the distance from the display screen to the user's eye under test.

The hash line images displayed on the screen may be configured to have a width between about 2 and 8 pixels and may have a width of about 2, 3, 4, 5, 6, 7, or 8 pixels on the screen. The radial line images displayed on the screen are configured to have a width between about 4 and 8 pixels and may have a width of about 4, 5, 6, 7, or 8 pixels on the screen. The length of the lines displayed on the screen are between about 40 and 60 mm long, or about 20 and 80 mm, about 30 and 70 mm, about 20 and 60 mm, about 30 and 60 mm, about 50 and 60 mm, and may be about 20, 30, 40, 45, 50, 55, 60, 65, 70, 80 mm long.

The system may comprise a duochrome image comprising a duochrome background image with at least two portions separated by an interface and an image overlaid on the duochrome background across the interface between the duochrome background portions, wherein each the image in each of the duochrome background portions is simultaneously imaged to an ocular foveal point of the user's eye under test.

The distance from the display screen to the user's eye under test may be determined from a live video stream of the user's eyes during a test.

According to a second aspect of the invention, there is provided a method for self-determination of eyeglass prescription for a user via a mobile computing device. The method may comprise the step of providing a mobile computing device. The mobile device may comprise a processor configured for executing program instructions stored in the non-volatile memory. The mobile device may further comprise a visual display screen adapted to receive image information from the processor to present instructions and images to a user. The mobile device may further comprise a camera configured to receive images of the user's pupils during a test situation. The method may further comprise the step of providing application program instructions for directing the processor to undertake a method for determining an eyeglass prescription. The program instructions may comprise program code for determining if an eye of the user is myopic. If the user's eye is myopic, the program instructions may further comprise program code for determining Principal and Axis Meridians of a user's eyes while the user is observing the image information on the display screen; and program code for calculating Sphere, Cylinder and Axis prescriptions from the Principal and Axis Meridians.

According to a particular arrangement of the second aspect, there is provided a method for self-determination of eyeglass prescription for a user via a mobile computing device, the method comprising:
providing a mobile computing device comprising:
a processor configured for executing program instructions stored in the non-volatile memory;
a visual display screen adapted to receive image information from the processor to present instructions and images to a user; and
a camera configured to receive images of the user's pupils during a test situation;
wherein the method comprises providing application program instructions for directing the processor to undertake a method for determining an eyeglass prescription, the program instructions comprising:
program code for determining if an eye of the user is myopic, and if the user's eye is myopic;
program code for determining Principal and Axis Meridians of a user's eyes while the user is observing the image information on the display screen; and
program code for calculating Sphere, Cylinder and Axis prescriptions from the Principal and Axis Meridians.

Determining if an eye of the user is myopic may comprise program code for displaying an image on the display screen comprising:
a duochrome background; program code for providing instructions to the user; and
program code for receiving input from the user with respect to a portion of the image which appears subjectively clearer to the user.
Determining the Axis Meridian may comprise:
program code for displaying a radially oriented image on the display screen; program code for providing instructions to the user; and
program code for receiving input from the user with respect to a portion of the radially oriented image which appears subjectively clearer to the user.
Determining the Principal Meridians may comprise:
program code for displaying a hash line image on the display screen comprising a duochrome background and receiving input from the user with respect to a location spaced from the users eye under test where the lines appears subjectively equally clear to the user; and
determining the distance from the display screen to the user's eye under test.

The method may comprise presentation of a duochrome image on the display screen, the duochrome image comprising a duochrome background with at least two portions separated by an interface and an image overlaid on the duochrome background across the interface between the duochrome background portions, wherein each the image in each of the duochrome background portions is simultaneously imaged to an ocular foveal point of the user's eye under test.

The distance from the display screen to the user's eye under test may be determined from a live video stream of the user's eyes during a test.

The duochrome background may comprise a background image having a first portion and a second portion and an interface wherein the first and second portions are adjacent each other.

The first portion may comprise a red background portion and the second portion may comprise a green or blue background.

The hash line image may be overlaid over both the red and green background portions and may be aligned between about 40 degrees to 90 degrees to the interface. The hash line image may be aligned between about 40° to 140° degrees, about 45° to 135° degrees, about 50° to 130° degrees, about 55° to 125° degrees, about 60° to 120° degrees, about 65° to 115°, about 70° to 110° degrees, about 75° to 105° degrees, about 80° to 100° degrees, or about 85° to 95° degrees, and may be about 40°, 45°, 50°, 55°, 60°, 65°, 70°, 75°, 80°, 85°, 86, 87, 88, 89, 89.5, 90°, 90.5°, 91°, 92°, 93°, 94°, 95°, 100°, 105°, 110°, 115°, 120°, 125°, 130°, 135°, or about 140° degrees to the interface.

The hash line image may be aligned approximately perpendicular to the interface.

According to a third aspect of the present invention, there is provided a system for enabling self-determination of eyeglass prescription for a user via a mobile computing device.

The device may comprise volatile and non-volatile memory for storing data. The device may further comprise a processor configured for executing program instructions stored in the non-volatile memory. The device may further comprise a visual display screen adapted to receive image information from the processor to present instructions and images to a user. The device may further comprise a camera configured to receive images of the user's pupils during a test situation.

The system may comprise application program instructions for directing the processor to undertake a method for determining an eyeglass prescription. The method may comprise a step of determining if an eye of the user is myopic, and if the user's eye is myopic. The method may comprise a further step of determining Principal and Axis Meridians of a user's eyes while the user is observing the image information on the display screen. The method may comprise a further step of calculating Sphere, Cylinder and Axis prescriptions from the Principal and Axis Meridians. The method may comprise a further step of displaying the calculated prescription values to the user.

According to a particular arrangement of the third aspect, there is provided a system for enabling self-determination of eyeglass prescription for a user via a mobile computing device, the device comprising:

volatile and non-volatile memory for storing data;
a processor configured for executing program instructions stored in the non-volatile memory;
a visual display screen adapted to receive image information from the processor to present instructions and images to a user; and
a camera configured to receive images of the user's pupils during a test situation;
wherein the system comprises application program instructions for directing the processor to undertake a method for determining an eyeglass prescription, the method comprising:
determining if an eye of the user is myopic, and if the user's eye is myopic;
determining Principal and Axis Meridians of a user's eyes while the user is observing the image information on the display screen;
calculating Sphere, Cylinder and Axis prescriptions from the Principal and Axis Meridians; and
displaying the calculated prescription values to the user.

The step of determining if an eye of the user is myopic may comprises a method implemented by execution of program instructions in the processor. The method may comprise:

displaying an image on the display screen comprising a first portion having a duochrome background;
providing instructions to the user; and
receiving input from the user with respect to a portion of the image which appears subjectively clearer to the user.

The step of determining the Axis Meridian may comprise a method implemented by execution of program instructions in the processor. The method may comprise:

displaying a radially oriented image on the display screen;
providing instructions to the user; and
receiving input from the user with respect to a portion of the radially oriented image which appears subjectively clearer to the user.

The step of locating the Principal Meridians may comprise a method implemented by execution of program instructions in the processor. The method may comprise:

displaying a hash line image on the display screen comprising a first portion having a duochrome background and receiving input from the user with respect to a location spaced from the users eye under test where the lines appear subjectively equally clear to the user; and determining the distance from the display screen to the user's eye under test.

The hash line images displayed on the screen may be configured to have a width between about 2 and 8 pixels and may have a width of about 2, 3, 4, 5, 6, 7, or 8 pixels on the screen. The radial line images displayed on the screen are configured to have a width between about 4 and 8 pixels and may have a width of about 4, 5, 6, 7, or 8 pixels on the screen. The length of the lines displayed on the screen are between about 40 and 60 mm long, or about 20 and 80 mm, about 30 and 70 mm, about 20 and 60 mm, about 30 and 60 mm, about 50 and 60 mm, and may be about 20, 30, 40, 45, 50, 55, 60, 65, 70, 80 mm long.

According to a fourth aspect of the present invention, there is provided a method for self-determination of eyeglass prescription for a user via a mobile computing device. The method may comprise the step of providing a mobile computing device comprising:

a processor configured for executing program instructions stored in the non-volatile memory;
a visual display screen adapted to receive image information from the processor to present instructions and images to a user; and
a camera configured to receive images of the user's pupils during a test situation.

The method may comprise the further step of providing application program instructions for directing the processor to undertake a method for determining an eyeglass prescription.

The program instructions may comprise program code for determining if an eye of the user is myopic, and if the user's eye is myopic. The program instructions may further comprise program code for determining Principal and Axis Meridians of a user's eyes while the user is observing the image information on the display screen. The program instructions may further comprise program code for calculating Sphere, Cylinder and Axis prescriptions from the Principal and Axis Meridians.

According to a particular arrangement of the fourth aspect of the present invention, there is provided a method for self-determination of eyeglass prescription for a user via a mobile computing device. The method may comprise the steps of:

providing a mobile computing device comprising:
a processor configured for executing program instructions stored in the non-volatile memory;
a visual display screen adapted to receive image information from the processor to present instructions and images to a user; and
a camera configured to receive images of the user's pupils during a test situation;
wherein the method comprises providing application program instructions for directing the processor to undertake a method for determining an eyeglass prescription, the program instructions comprising:
program code for determining if an eye of the user is myopic, and if the user's eye is myopic;
program code for determining Principal and Axis Meridians of a user's eyes while the user is observing the image information on the display screen; and
program code for calculating Sphere, Cylinder and Axis prescriptions from the Principal and Axis Meridians.

The step of determining if an eye of the user is myopic may comprise program code for displaying an image on the display screen comprising:
   a duochrome background;
   program code for providing instructions to the user; and
   program code for receiving input from the user with respect to a portion of the image which appears subjectively clearer to the user.

The step of determining the Axis Meridian may comprise:
   program code for displaying a radially oriented image on the display screen;
   program code for providing instructions to the user; and
   program code for receiving input from the user with respect to a portion of the radially oriented image which appears subjectively clearer to the user.

The step of determining the Principal Meridians may comprise:
   program code for displaying a hash line image on the display screen comprising a first portion having a duochrome background and receiving input from the user with respect to a location spaced from the users eye under test where the lines appear subjectively equally clear to the user; and
   determining the distance from the display screen to the user's eye under test.

The present disclosure relates generally to a system and method for determining the refractive error of a patient, more particularly determining the patient's refractive error by using a mobile computing device, and providing the patient with a corrective lenses prescription for the patient's preferred type of corrective lenses. The system and method do not require the trip or expense of a doctor visit, and are optimized for convenience and cost effectiveness.

In a general embodiment, the present disclosure provides a method for determining a corrective lenses prescription of a patient. The method includes, separately, for each eye of the patient, determining the astigmatism prescription of the patient via a computerized screen.

In a further embodiment, the first diagram and the second diagram are a same diagram. In an alternative further embodiment, the first diagram and the second diagram are different diagrams.

In an alternative embodiment, the present disclosure provides a method for determining a corrective lenses prescription of a patient. The method includes, separately, for each eye of the patient, determining the astigmatism prescription of the patient, and determining the power of the corrective lenses prescription of the patient through the presentation of images on the display screen of a mobile device, receiving input from the user with respect to the displayed images, and determination of the distance between the mobile device display screen and the patient's eye or eyes.

In a further embodiment, the method also includes, separately, for each uncorrected eye of the patient, determining whether the patient is nearsighted or farsighted by presenting an image to the patient via the display screen of the mobile device, the image being presented to the patient comprising a as least on region having a duochrome background and further enabling the patient provide an input to the mobile device corresponding to part of the image as presented on the screen correlating to a region that the user considers to be the most clear.

In another embodiment, the present disclosure provides a non-transitory computer readable medium. The non-transitory computer readable medium includes a plurality of instructions, which when executed by at least one processor, cause the at least one processor to operate with at least one display device of a mobile device, at least one memory device of the mobile device, at least one user input device, and at least one camera device to determine a corrective lens prescription of the patient.

The duochrome background of any of the above aspects may comprise a background image having a first portion and a second portion and an interface wherein the first and second portions are adjacent each other.

The first portion may comprise a red background portion and the second portion may comprise a green or blue background.

The hash line image may be overlaid over both the red and green background portions and is aligned between about 40 degrees to 90 degrees to the interface.

The hash line image may be aligned approximately perpendicularly to the interface.

An advantage of the present disclosure is to provide a patient more convenience in determining and receiving a glasses and/or contact lens prescription.

An advantage of the present disclosure is to reduce the cost and expense to the patient of determining and receiving a glasses and/or contact lens prescription.

Another advantage of the present disclosure is to determine a glasses and/or contact lens prescription without the need for expensive equipment only feasible for use in an optometry specialty practice.

Another advantage of particular embodiments of the present disclosure is to determine a glasses and/or contact lens prescription without placing lenses before the eyes of the patient.

Still another advantage of the present disclosure is to more quickly determine a glasses and/or contact lens prescription.

Further advantages of the systems and methods disclosed herein include, but are not limited to:
   An automatic calibration process by which the environmental lighting is assessed, and the device display brightness is adjusted.
   An automatic calibration process by which the pupillary distance is calculated. The pupillary distance may be used in the process of calculating the user's refractive state. The pupillary distance may be made available to the user, so as the user may use this value to order prescription glasses.
   History and symptoms data collection, which can be used for best prescription prediction algorithms.
   Determination of the refractive state of the user's eyes, specifically, the optical system Sphere, Cylinder, and Cylinder Axis corrective requirements for each eye.
   A subjective method of obtaining the refractive state of the user's eyes.
   Longitudinal recording of refractive results over time, enabling the comparison over time of the results.
   Artificial intelligence and machine learning based analysis/algorithms to provide more accurate results.
   An objective method of obtaining the refractive state of the user's eyes.
   A method of evaluating the accommodative function, and obtaining the Near Addition component of a glasses or contact lens prescription for the user's eyes.
   Algorithms to provide best prescription predictions.
   An efficient method for obtaining 1st Purkinje image data, for example, utilising the display screen of a mobile computing device to generate a bright 'flash' to produce a reflection off the user's cornea, which is then captured by the camera system of the device.

Methods for evaluating binocular vision function, for example using pupil tracking functionality of the software application to monitor the relative location of the individual pupils and determine if separation anomalies can be detected, thus indicating binocular dysfunction of the user's eyes.

Methods for evaluating Colour Vision, e.g. by inclusion of program code in the software application for implementation of the Ishihara Colour Test as would be appreciated by the skilled addressee.

Methods for evaluating Macula function e.g. by inclusion of program code in the software application for implementation of the Amsler grid Test as would be appreciated by the skilled addressee.

Methods for evaluating Anterior eye pathology, for example, utilising the camera system of the mobile computing device to capture images of the anterior eye, and using algorithms to analyse these images to detect various pathology, for example infection, advanced cataract, eyelid tumours.

Methods for evaluating the Visual Field e.g. utilising a simple automated perimetry routine as would be appreciated by the skilled addressee Methods for evaluating some Neurological disorders of the visual system e.g. by inclusion of program code in the software application for assessing eye movement in different directions to diagnose various nerve lesions. Additionally, examination of the user's pupil reflexes and pupillary responses can be analysed for neurological defects as would be appreciated by the skilled addressee.

Specific integrated module for automated ophthalmic medications tracking and reporting.

Additional features and advantages are described herein, and will be apparent from the following Detailed Description and the Figures.

BRIEF DESCRIPTION OF THE DRAWINGS

Notwithstanding any other forms which may fall within the scope of the present invention, a preferred embodiment/preferred embodiments of the invention will now be described, by way of example only, with reference to the accompanying drawings in which.

DEFINITIONS

Figure 1:
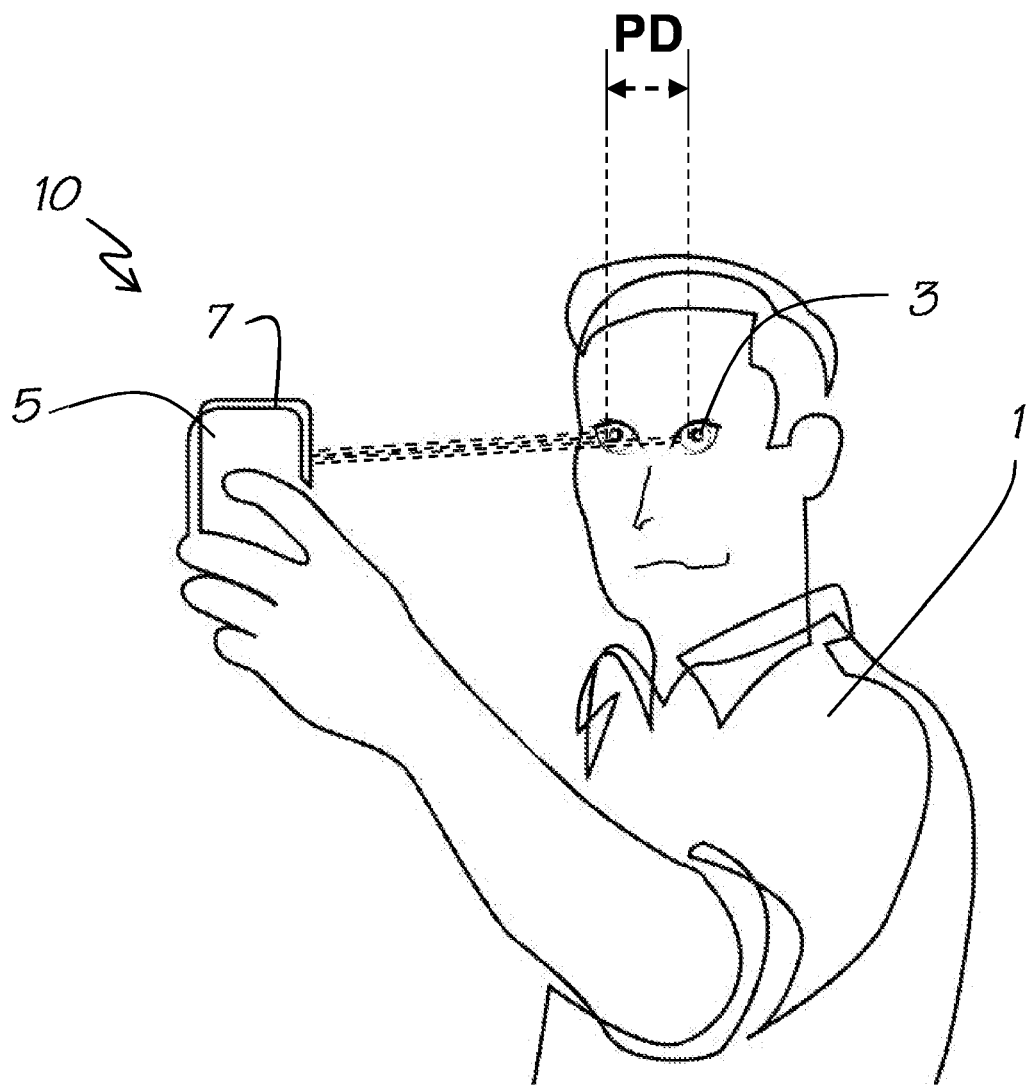
FIG. 1 shows a schematic depiction of a use case of a DIY prescription application via a mobile computing device.

The following definitions are provided as general definitions and should in no way limit the scope of the present invention to those terms alone but are put forth for a better understanding of the following description.

Unless defined otherwise, all technical and scientific terms used herein have the same meaning as commonly understood by those of ordinary skill in the art to which the invention belongs. It will be further understood that terms used herein should be interpreted as having a meaning that is consistent with their meaning in the context of this specification and the relevant art and will not be interpreted in an idealized or overly formal sense unless expressly so defined herein. For the purposes of the present invention, additional terms are defined below. Furthermore, all definitions, as defined and used herein, should be understood to control over dictionary definitions, definitions in documents incorporated by reference, and/or ordinary meanings of the defined terms unless there is doubt as to the meaning of a particular term, in which case the common dictionary definition and/or common usage of the term will prevail.

For the purposes of the present invention, the following terms are defined below.

The articles "a" and "an" are used herein to refer to one or to more than one (i.e. to at least one) of the grammatical object of the article. By way of example, "an element" refers to one element or more than one element.

The term "about" is used herein to refer to quantities that vary by as much as 30%, preferably by as much as 20%, and more preferably by as much as 10% to a reference quantity. The use of the word 'about' to qualify a number is merely an express indication that the number is not to be construed as a precise value.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Any one of the terms: "including" or "which includes" or "that includes" as used herein is also an open term that also means including at least the elements/features that follow the term, but not excluding others. Thus, "including" is synonymous with and means "comprising".

In the claims, as well as in the summary above and the description below, all transitional phrases such as "comprising", "including", "carrying", "having", "containing", "involving", "holding", "composed of", and the like are to be understood to be open-ended, i.e. to mean "including but not limited to". Only the transitional phrases "consisting of" and "consisting essentially of" alone shall be closed or semi-closed transitional phrases, respectively.

As used herein, the term "exemplary" is used in the sense of providing examples, as opposed to indicating quality. That is, an "exemplary embodiment" is an embodiment provided as an example, as opposed to necessarily being an embodiment of exemplary quality serving as a desirable model or representing the best of its kind.

Although any methods and materials similar or equivalent to those described herein can be used in the practice or testing of the present invention, preferred methods and materials are described. It will be appreciated that the methods, apparatus and systems described herein may be implemented in a variety of ways and for a variety of purposes. The description here is by way of example only.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g. a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phrase "and/or", as used herein in the specification and in the claims, should be understood to mean "either or both" of the elements so conjoined, i.e. elements that are conjunctively present in some cases and disjunctively present in other cases. Multiple elements listed with "and/or" should be construed in the same fashion, i.e. "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e. the inclusion of at least one, but also including more than one, of a number or list of elements, and, optionally, additional unlisted items. Only terms clearly indicated to the contrary, such as "only one of" or "exactly one of", or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either", "one of", "only one of", or "exactly one of". "Consisting essentially of", when used in the claims, shall have its ordinary meaning as used in the field of patent law.

As used herein in the specification and in the claims, the phrase "at least one", in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B", or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

For the purpose of this specification, where method steps are described in sequence, the sequence does not necessarily mean that the steps are to be carried out in chronological order in that sequence, unless there is no other logical manner of interpreting the sequence.

In addition, where features or aspects of the invention are described in terms of Markush groups, those skilled in the art will recognise that the invention is also thereby described in terms of any individual member or subgroup of members of the Markush group.

DETAILED DESCRIPTION

A user interface and a corresponding method of user interaction are disclosed. In the following description, specific details are presented in order to provide a thorough understanding of the embodiments of the present invention. It will be apparent, however, to a person skilled in the art that these specific details need not be employed to practice the present invention. Conversely, specific details known to the person skilled in the art are omitted for the purposes of clarity where appropriate.

It should be noted in the following description that like or the same reference numerals in different embodiments denote the same or similar features.

Methods of remotely and autonomously measuring the human eye's refractive state have the potential to greatly reduce the time and cost required to obtain a spectacle prescription for a user. This potential can only truly be realised if the user does not need any specialised training (or does not need assistance from someone who has received the specialist training), and is achievable in a natural, accessible and immediate way. The commercial potential for any DIY spectacle prescription system is reduced if the consumer faces technical or usability barriers, such as a lengthy and difficult process, the need to visit a fixed location, the need for dedicated equipment or apparatus, or a complex user interface.

An ideal system of DIY prescription determination would have no difficult or time-consuming setup, must generate accurate and reliable results, and should be deployed on widely available consumer hardware, such as mobile devices e.g. smartphones or personal tablet computing devices. Additionally, the system should also make the results available to the subject in real time, with little effort, and be stored within the system with means for easy extraction of the calculated prescription at a later stage, e.g. when the user is placing an order for prescription spectacles or consulting with a specialist for further vision-related investigations.

To maximise the accessibility of such a system to consumers, the system ideally would also be capable of performing in a typical consumer environment, such as in the home or outdoors, and therefore would necessarily be able to operate with very few constraints on lighting conditions, image resolution or the user's position or posture when using the system.

Additionally, the overall system must be able to seamlessly obtain basic measurements which are required for the spectacle ordering and manufacturing process, namely, pupillary distance. In particular arrangements, the pupillary distance may be either pre-stored in the software application or the application may be configured to receive input from the user of their specific pupillary distance wherein the application may guide the user via instructions displayed on the display screen of the mobile device. For example, the user may be directed to place the camera of the mobile device a known distance, d (refer to FIG. 8), from the user's eyes and the pupillary distance can be calculated via similar triangles as discussed in greater detail below with reference to FIG. 8. In particular examples, the user may be directed to set the distance, d, using a ruler, or alternatively, an object of known size, such as e.g. a sheet of A4 size paper A system for DIY prescription determination may be carried out using either subjective or objective approaches, however, the limitations of both approaches present difficulties in realisation of a reliable system. For example:

Subjective tests require feedback from the user as to which presented images are preferred. However, subjective testing can give sufficiently erroneous results for various reasons, for example: accommodation of the user's eye (i.e. ability or inability of the eye to change its focus from distant to near objects and vice versa); the user not following instructions correctly, or the user having a preference for a particular shape over another, among various other reasons as would be appreciated by the skilled addressee.

Objective tests do not take into account how the brain perceives and analyses the images received by the ocular system. Therefore, these tests often do not provide the best prescription for all patients, as some patients prefer results skewed towards a subjective result.

A suitably skilled clinician therefore often considers both subjective and objective results when determining the final spectacle prescription.

Accordingly, for a self-test spectacle prescription system to be effective, it must be easy for the user to understand the step of the tasks used to determine their visual refractive status and it must be easy for the user to perform those tasks satisfactorily in order to provide an accurate description of the user's current visual refractive status with consideration of user input sufficient to enable ordering of prescription spectacles for correction of the user's vision.

The systems and methods disclosed herein for determining a user's eyeglass prescription is adapted to utilise a software application adapted to be executed on a mobile computing device, comprising for example a smartphone or tablet device comprising a display screen and at least one camera device configured to be directed towards a user when the user is viewing the display screen (for instance, a forward-facing camera typically provided on modern mobile computing devices for example to be utilised in a video (e.g. FaceTime®—a trademark of Apple Inc.) call. The software application is configured to provide visual stimulus to the user to determine, or to estimate, a person's refractive status. The software application is designed to produce a useful optical prescription that can be used to order optical appliances such as spectacles and or contact lenses, by using the invention as a smartphone application thus providing the significant advantage that a user can receive a determination of their individual eyeglass prescription without the requirement of visiting a qualified optical professional nor the use of highly specialised optometry equipment for assessment of their refractive status such as a phoropter.

In a particular arrangement 10 of the system as depicted in use in FIG. 1, a user 1 with eyes 3 requiring refractive correction executes a software application on a mobile computing device 5 for example, a smartphone or tablet computing device or similar with a display screen 7 as would be appreciated by the skilled addressee. The mobile device comprises a visual display screen 7 for presentation of instructions and visual images to the user. In preferred arrangements, the device 5 display screen is a touch sensitive device adapted for receiving input from user 1 in response to the instructions and/or images displayed on the display screen. Mobile device 5 further comprises at least one forward facing camera such that user's eyes 3 are in the field of view of the camera when user 1 is looking at the display screen of device 5. User's eyes 3 are separated by a distance PD which, in use is typically designated to be the inter-pupillary distance of user's eyes 3 i.e. the horizontal distance between the pupils of the user's left and right eyes.

Figure 2:
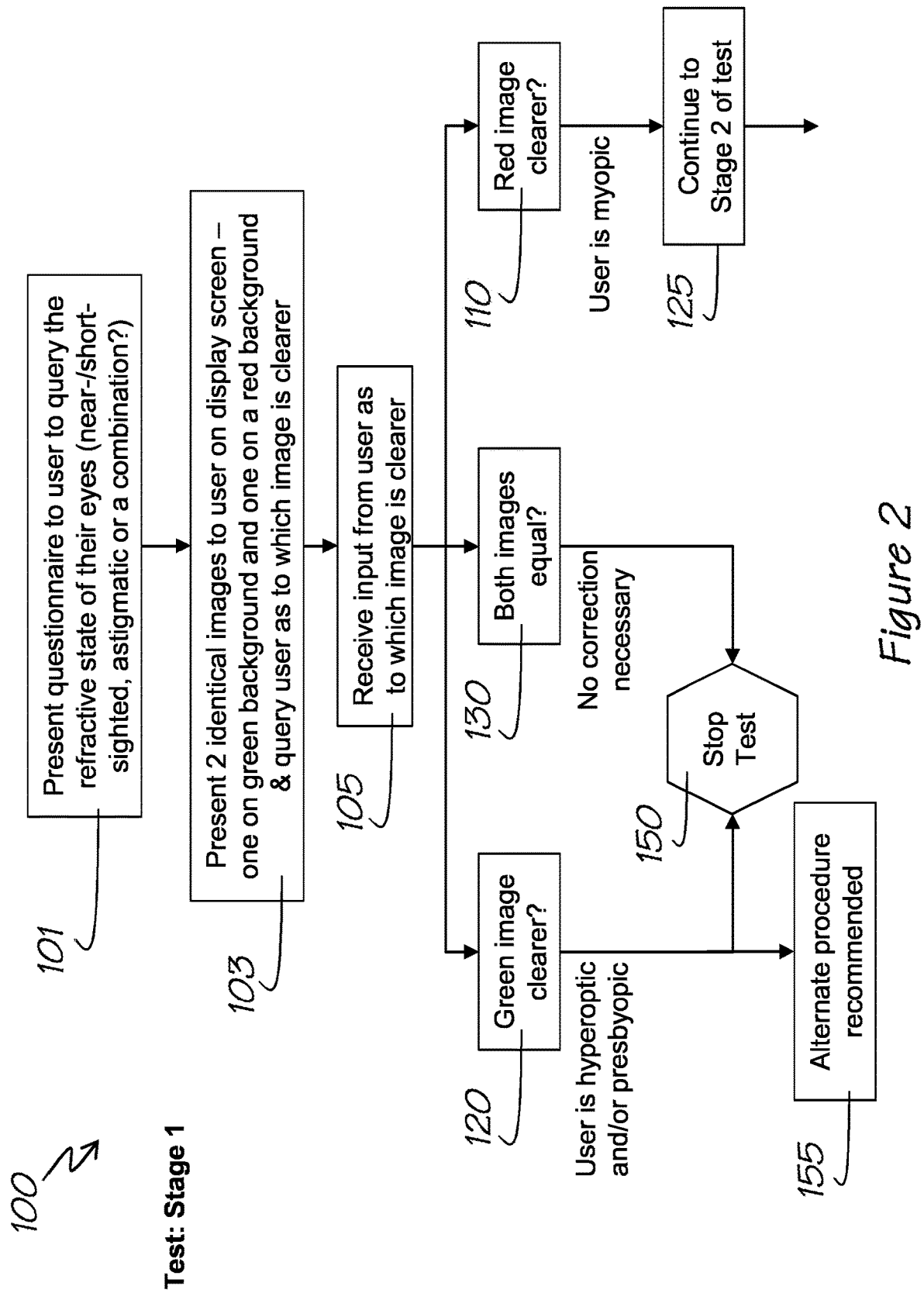
FIG. 2 shows a flowchart illustrating an example initial stage of a method of operating an embodiment of the system of the present disclosure.
Figure 3:
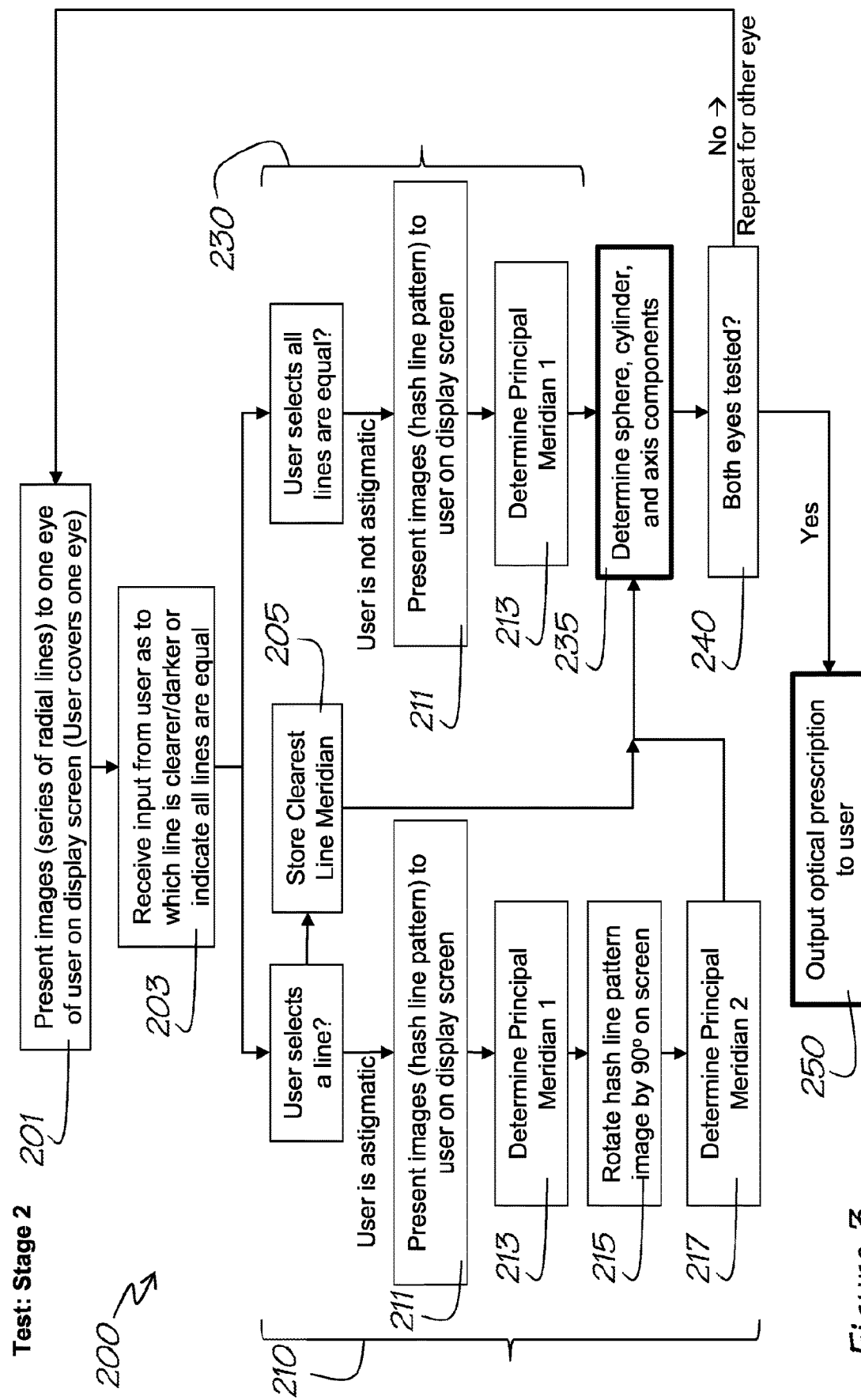
FIG. 3 shows a flowchart illustrating an example method of a further stage of a method of operating an embodiment of the system of the present disclosure.
Figure 4:
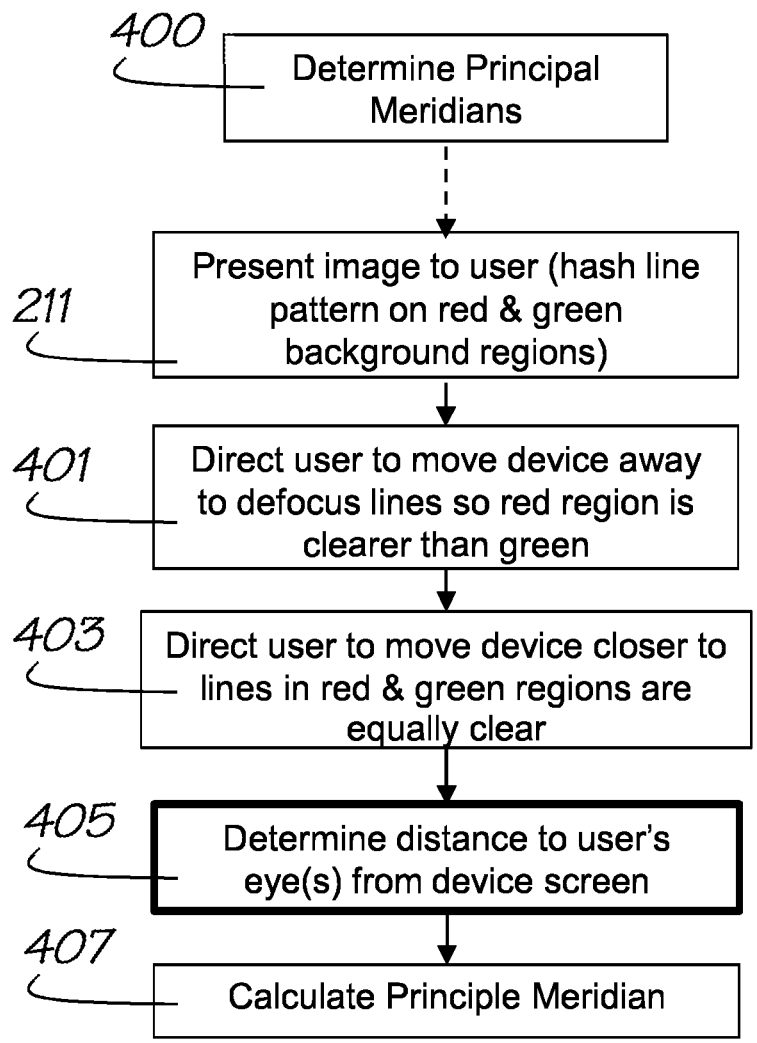
FIG. 4 shows a flowchart illustrating an example method of a detail stage of a method of operating an embodiment of the system of the present disclosure for determining Principal Meridians for a calculation of a patient's eyeglass prescription.

FIGS. 2 to 4 illustrate flowcharts of an example of various stages of processes or methods according to a particular embodiment of the system of the present disclosure. In various embodiments, one or more processors execute a set of instructions to implement the processes. Although the processes are described with reference to the flowcharts shown in FIGS. 2 to 4, the system may employ many other processes of performing the acts associated with these illustrated processes. For example, the system may change the order of certain of the illustrated blocks. The system can also make certain of the illustrated blocks optional, the system may repeat certain of the illustrated blocks, and/or the system may not employ certain of the illustrated blocks in accordance with requirements.

FIG. 2 illustrates a flowchart of an initial stage 100 of a method for self-determination of eyeglass prescription via mobile devices and generally related to determining a spectacle and/or a contact lens prescription for a patient with a refractive error in one or both eyes in need of correction to restore the patient's visual acuity.

Initially the software application as adapted to execute the methods and processes disclosed herein are configured to request the user to provide initial input data which may be of assistance in calculating the user's eyeglass prescription. For example, the software application may be adapted to ask the user a series of questions 101 in order to initially help determine whether they are myopic, hyperopic, astigmatic, presbyopic, or a combination of these. This information can be used to direct the exam pathway utilising the particular methods available as discussed below.

Figure 5:
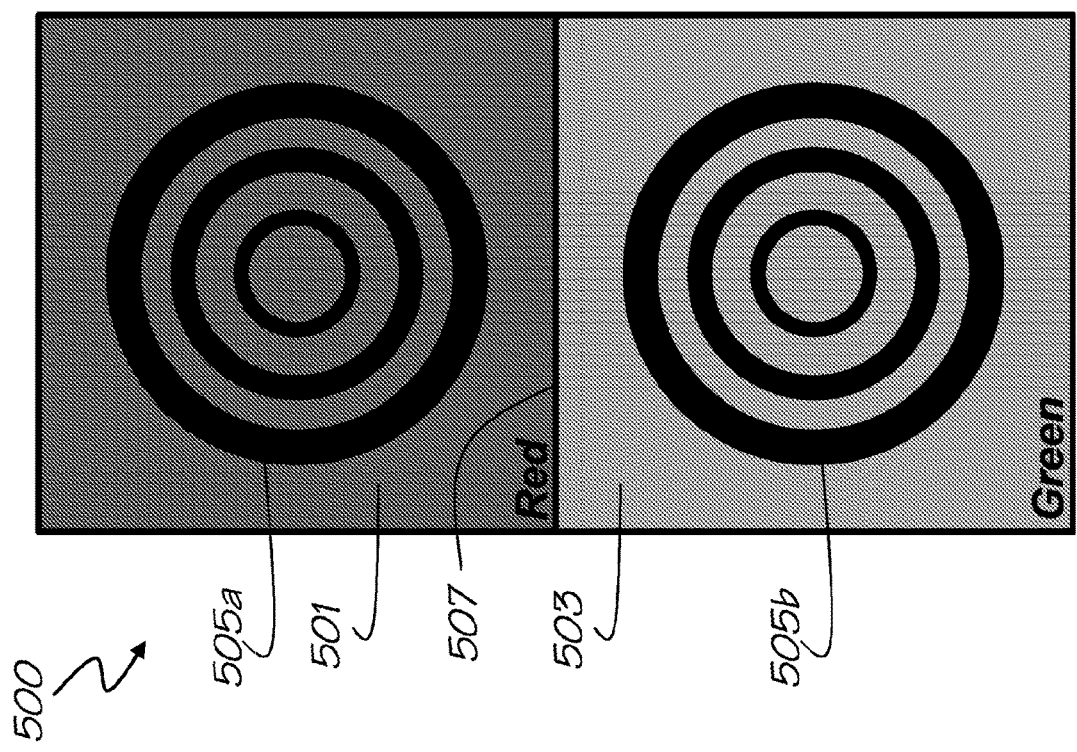
FIG. 5 illustrates a screen shot of an example of an embodiment of the system of the present disclosure, wherein the system displays an image in relation to an initial stage of the method of operating an embodiment of the system of the present disclosure.

To start the test (Step 1), the software application is adapted to display 103 an image 500 on the display screen of mobile device 5 wherein the image comprises two equal images 505 (for example Verhoeff's Circles), displayed on a duochrome background comprising two adjacent background regions 501 and 503 having an interface 507 where one image 505*a* is displayed on a red background 501, and one 505*b* on a green background 503 (although a blue background may also be used instead of green), for example as shown in FIG. 5 and is asked which one appears clearer. In the accompanying drawings (e.g. FIG. 5 and others), the red and green portions (e.g. 501 and 503) of the duochrome background are depicted for clarity in as also displaying the descriptors "Red" and "Green" in the corresponding portions, however, it will be appreciated that the image 500 presented to the user on screen 7 of mobile device 5 would generally not include such descriptors.

In particular arrangements, the software application may present an instruction to the user on the display screen e.g. "Which image is clearer?" and present a plurality of options for response by the user in the form of a corresponding plurality of designated touch regions of the display screen for the user to provide input 105 to the software application. Example response options provided to the user may include "Red", "Green" and "Neither". If the user indicates that the image on the red background is clearer 110, then it will be initially assumed that the user is myopic, and the user will progress to the next stage of the method, method 200 as illustrated in FIG. 3.

The thickness and spacing of the lines of the Verhoeff's Circles 505 in the displayed images is generally not significant, the primary factor in the success of the test being that the user is able to identify whether they are clearer on a red or green background. As visual acuity is not measured, nor is it a design requirement for success, there is no requirement for the user to identify any detail in the circle images. As long as the user can see the circles, it is sufficient. This is usually possible for all users, and simply moving the mobile device closer or further away allows virtually all users to see the circles with sufficient clarity to make an initial assessment of whether or not the user is myopic.

The presentation of identical images on a duochrome (e.g. red and green) background (e.g. image 500 of FIG. 5) comprises a duochrome test which utilises the wavelength-dependent properties of the focussing power of the lens of the user's eyes thus making use of the transverse chromatic aberration of the eye. Because of the chromatic aberration of the eye, the shorter wavelengths (green) are focused in front of the longer red wavelengths. If the user indicates that neither image in the red or green regions is clearer than the other, it will be assumed that the user's eye does not require correction and the test will stop 150.

For instance, if the user, when presented with image 500 on screen 7 of the mobile device 5 indicates that the image 505*b* in the green region 503 is clearer, it will be assumed that the user either or additionally is hyperopic, or presbyopic, whereupon the method 100 will stop the test 150 and the user may be guided 155 by the software application to an alternative test procedure as either no correction is necessary or the method 100 is not able to provide a prescription for correction of the user's specific refractive error. If the user indicates that image 505*a* in the red portion 501 of image 500 is clearer, then the user is determined to be myopic and mothed 100 proceeds 125 to Stage 2 of the test (method 200 as shown in FIG. 3).

Figure 6A:
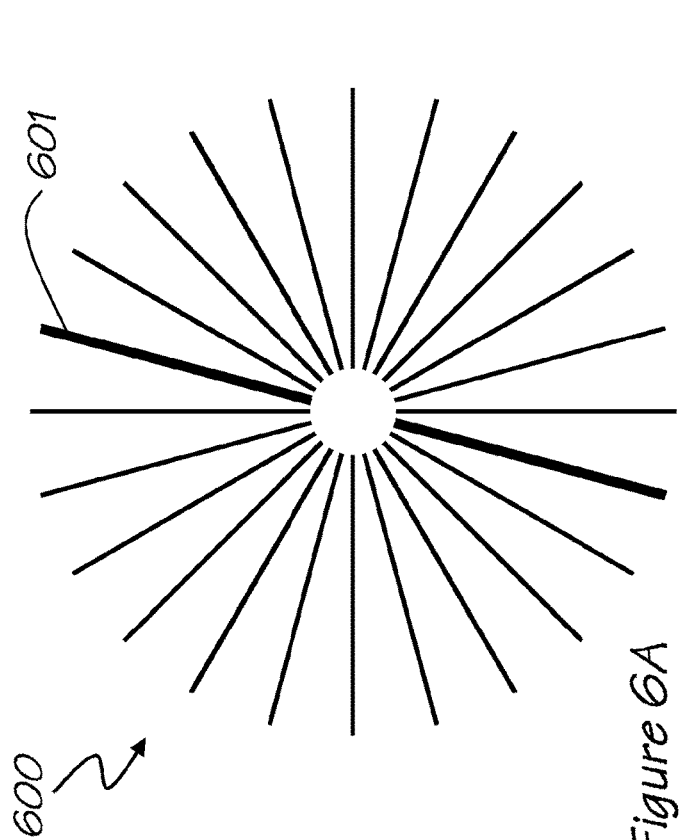
FIG. 6A illustrates a screen shot of an example of an embodiment of the system of the present disclosure, wherein the system displays a further image in relation to a further stage of the method of operating an embodiment of the system of the present disclosure for the patient to provide an input wherein the input corresponds to a Clearest Line Meridian relating to an Axis measurement of the patient.

FIG. 3 shows a flowchart illustrating an example method 200 of a further stage (Step 2) of a method of operating an embodiment of the system of the present disclosure. After determining in the Stage 1 method 100 that the user requires visual correction of myopia in at least one eye 3, the software application is configured to present 201 a further image to the user on the display screen of mobile device 5. For step 201, the image comprises a series of radial lines as depicted in FIG. 6A and to observe which, if any, of the lines appears clearer/darker than the others. In radial line image 600 as shown in FIG. 6A, line 601 is represented as a darker line to represent the apparent image that may be observed by a user with astigmatism in one eye having an Axis of approximately 15°. In the image 600 that is presented to the user on the display screen 7 all the radial lines are presented with equal thickness. The user is directed through instructions presented on the screen to move the mobile device 5 nearer to or further away from their eyes in order to recognise if any of the lines are indeed clearer. The user is asked to either select the clearest line via the touch sensitive display or otherwise indicate via a designated touch surface (or location on the touch sensitive display interface) that all lines appear to be of equal clarity (or that, no particular line is clearer than any others in the image).

If the user selects a line in the image the method assumes that the user's eye requires correction for astigmatism and proceeds with sub-method 210. If, instead, the user indicates that all lines appear of equal clarity, the method assumes that the user's eye does not require correction for astigmatism and proceeds with sub-method 230.

Astigmatic Eye—Method 210

If input received 203 from the user indicates a selected line of the image presented in step 201, then the software application stores the rotational angle of the selected line as a Clearest Line Meridian into volatile or short-term memory of the mobile computing device 5 and then proceeds with sub-method 210 depicted in FIG. 3.

Figure 6B:
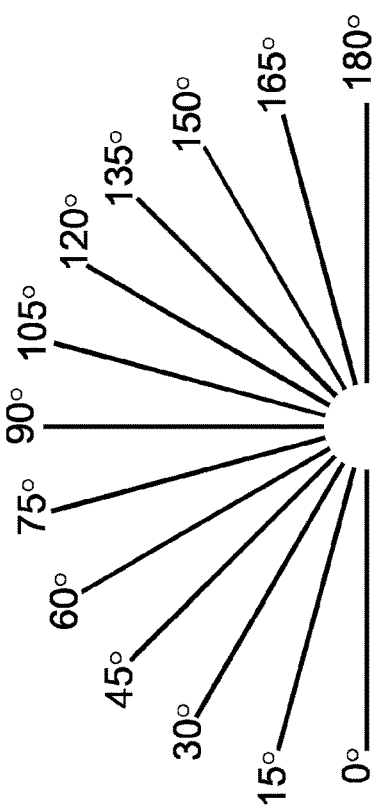
FIG. 6B illustrates the numbering convention used in the calculation of the Axis parameter in the eyeglass prescription from the image displayed in FIG. 6A.

The software application calculates the Axis parameter of the eyeglass prescription from the Clearest Line Meridian with reference to the conventional angular numbering of FIG. 6A. If, for example, the user selects a line equivalent to that with an angle (FIG. 6B) between 0° and 90°, then the Axis is designated as selected line plus 90 e.g. if the user selects the 30° line, then the Axis is reported as 30+90=120. If, alternatively, the user selects a line equivalent to that with an angle (FIG. 6B) between 90° and 180°, then the Axis is designated as selected line minus 90 e.g. if the user selects the 165° line, then the Axis is reported as 165−90=75.

The software application can report a compensated axis if required by applying adjustments to the reported Axis based upon the orientation of mobile computing device 5. If, for example, the user selects the 30° line whilst holding the mobile computing device 5 in a rotated orientation of 10° clockwise (as viewed by the user), then the compensated Axis will be reported as 120+10=130°. If, alternatively, the user selects the 30° line whilst holding the mobile computing device 5 in a rotated orientation of 10° counter clockwise (as viewed by the user), then the compensated Axis will be reported as 120−10=110°.

Figure 7C:
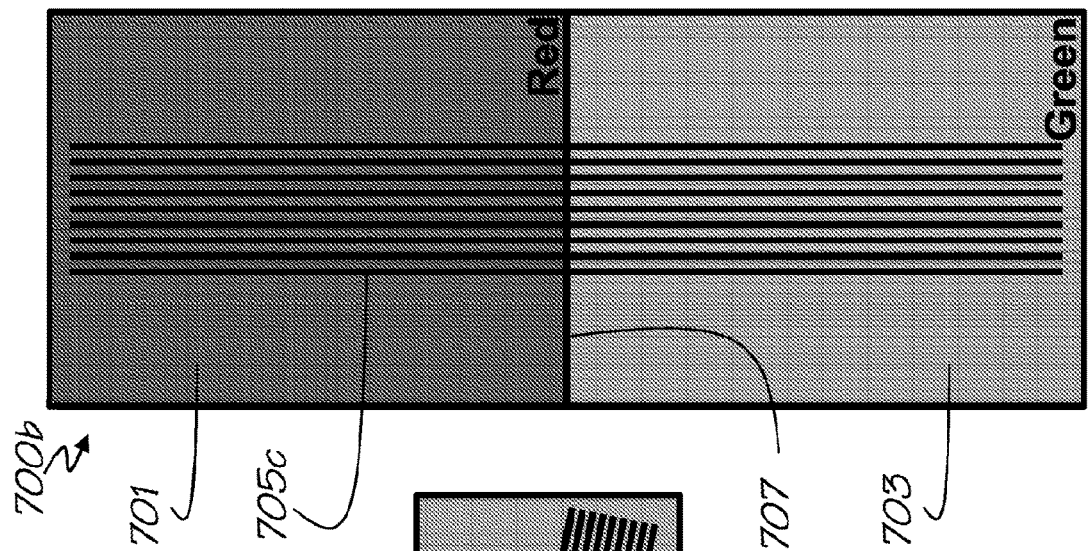
FIGS. 7A to 7C illustrate example screen shots of an example embodiments of the system of the present disclosure, wherein the system displays a Simultaneous Spilt Point Focus (SSPF) image for determining Principal Meridians for a calculation of a patient's eyeglass prescription according to a method of operating an embodiment of the system of the present disclosure.
Figure 7B:
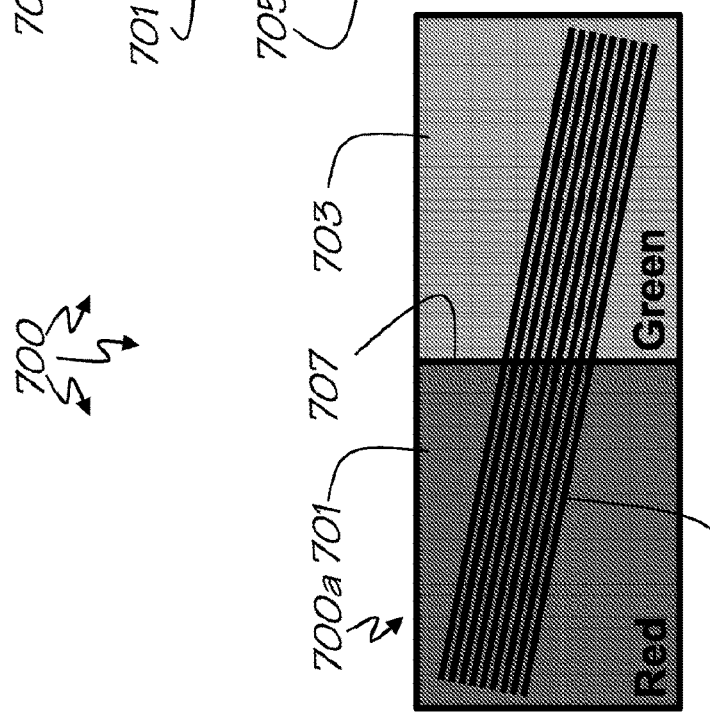
Figure 7A:
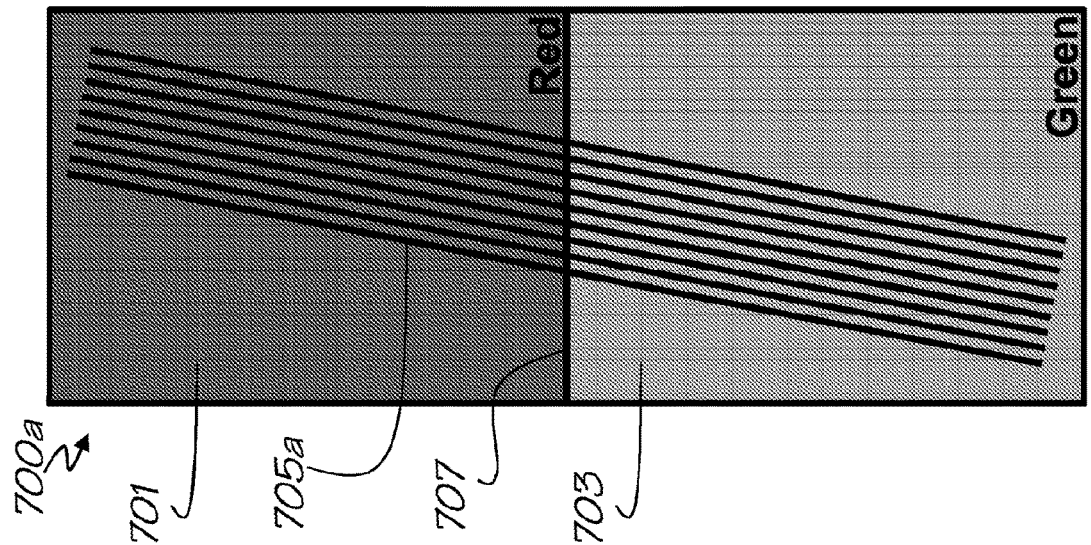

Initially, in sub-method 210, the software application presents 211 the user with a Simultaneous Spilt Point Focus (SSPF) image (described in further detail below) on the display screen comprising a hash line pattern 705A as depicted in FIG. 7A which in some embodiments, is oriented at the same angle of the radial line selected in step based on the input from step 203. In alternate embodiments, the user is presented with image 700c as shown in FIG. 7C where the hash line image 705c is oriented at or near 90 degrees (perpendicular) to the interface 707 between red/green background portions 701 and 703 respectively. In particular arrangements, a portion of the image 700 (shown in two arrangements 700a and 700b and alternate embodiment 707c) of FIGS. 7A to 7C is provided with a duochrome background comprising a red background portion 701 and a green (or blue) background portion 703 as a further duochrome test as discussed above. The user is prompted through instructions 213 on the display screen to carry out the Principal Meridian determination method 400 illustrated in FIG. 4 as discussed below to determine a first Principal Meridian (Meridian 1) to be used in the calculation of the Sphere component of the eyeglass prescription.

The thickness and spacing of the lines of the hash line pattern in the displayed images is determined with reference to the typical natural retinal cell spacing/density of the human eye, and the angular region subtended by the displayed image across the macula and perimacular regions (i.e. around the macular) of the eye at typical user distances, typically of about 1 m corresponding loosely to arm's length in accordance to the usage of the software application to administer the eye test. In particular arrangements, the software application may be configured with the assumption that the maximum working distance is about 1 m from the user's face. If the user is using the device to conduct the eye test program at a working distance, d, of between about 1 and 2 m (i.e. between −0.5D and −1.00D), the software application can make an adequate guess of the Principal Meridian values measurements (as discussed above) to within 0.5D accuracy for example by simply prescribing a correction of −0.50D, and the resulting prescription will be within/greater than 0.5D accuracy), and mostly within 0.25D accuracy, hence the need for accurate measurements of the distance between the device and the user's eyes beyond 1 m is unnecessary. For working distances, d, of between about 1 m and 67 cm (i.e. between −1.00D and about −1.50D, a similar strategy is appropriate, however, it is useful to obtain a true measurement as often as possible to eliminate an additional step in the methods disclosed herein for guessing an appropriate prescription correction value.

In particular arrangements, the lines of the images displayed to the user on the display screen 7 of the mobile device 5 of the systems and methods disclosed herein, are about 4 pixels wide, but may be configured to be between about 4 and 8 pixels wide. It has been noted that line widths of less than 3 pixels are usually ineffective. In particular arrangements, the lines may be configured to be either 4, 5, 6, 7, or 8 pixels wide, and preferably about 6 pixels wide, in accordance with requirements. In a mobile device having a display screen with pixel spacing of about 50 mm, a line on the display spanning a width of about 6 pixels will display as a line on the display being about 0.3 mm in width. Similarly, the lines of the radial image used for determination of any astigmatism axis see FIG. 6A), the lines on the display screen 7 of mobile device 5 may be between about 2 and 8 pixels wide. In particular arrangements, the radial lines may be configured to be either 2, 3, 4, 5, 6, 7, or 8 pixels wide, and preferably about 5 or 6 pixels wide, in accordance with requirements. As screen resolution (undoubtedly) increases over time, a correction factor will need to be added for future versions, so that the mm value is used rather than the pixel value. In particular arrangements, the lines displayed on display screen 7 by the software application may have anti-aliasing applied. Typically the lines of the hash line images (e.g. see FIGS. 7A to 7C) are chosen to be between about 40 and 60 mm long, and may be about 40 mm, 45 mm, 50 mm, 55 mm, or about 60 mm long, and preferably about 50 mm long, when displayed on the screen of the mobile device 5. It will be appreciated by the skilled addressee that the resulting physical size of the lines alters a little depending on the screen size and pixel density of the particular mobile device 5 in use, however, they remain constant enough to be effective across the range of devices presently available.

The hash line screen is a unique design taking advantage of the duochrome phenomenon described above, and further refining the presentation to obtain high image location accuracy that does not require nor allow the eye to change focus (also known as the eye's ability to accommodate)

during evaluation of the adjacent sides of the image. The duochrome image presented on the screen 7 of the user's mobile device 5 comprises a duochrome background image comprising at least two background portions separated by an interface, and an image overlaid upon the duochrome background portions across the interface between background regions. Each background region of the duochrome background comprises a different solid colour wherein the colours of adjacent background portions are sufficiently separate enough in colour (wavelength) such that there is a discernible difference in the focal point at which the user's eye focuses each colour towards the user's retina for example, one background portion may be either Blue or Green, whereas the adjacent portion may be Yellow or Red. In the presently described arrangement, both presentations (constituent images), or sides of the duochrome image (i.e. each of the one or more background positions), are simultaneously imaged to the ocular foveal point of the user's eye under test. This particular arrangement has not been described previously and is termed herein as the Simultaneous Spilt Point Focus (SSPF) design.

Figure 11A:
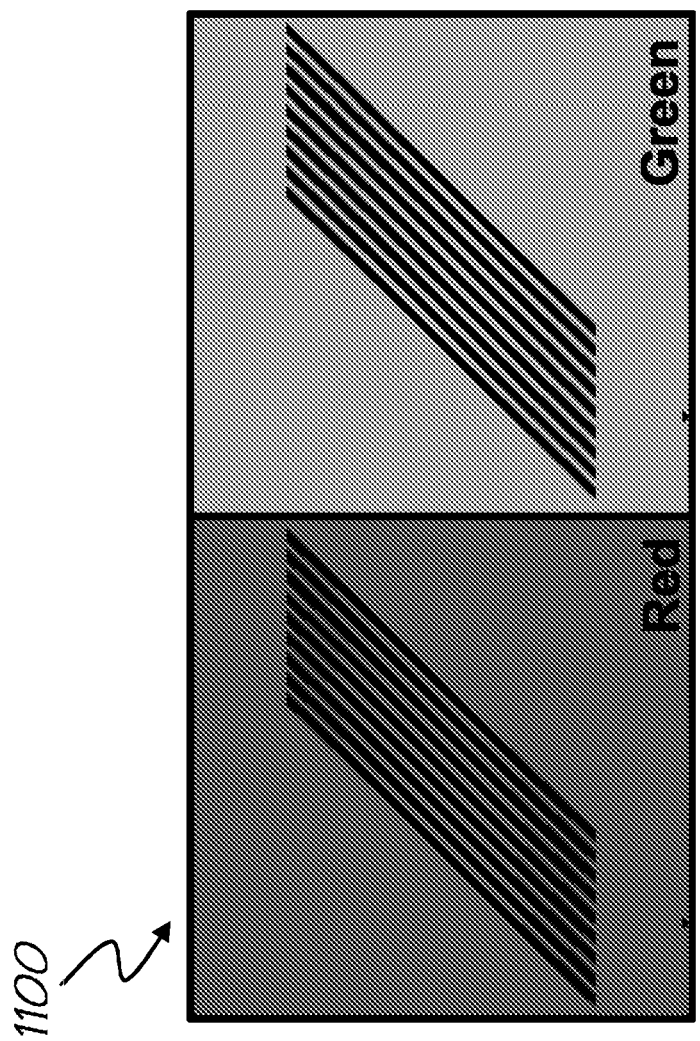
FIG. 11 shows a prior art known configuration of a traditional prior art, side-by-side duochrome eye test image.

Whilst the use of a duochrome image 1100 (similar to image 500 of FIG. 5) including red portion 1101 and green portion 1103 segments shown in FIG. 11 containing hash lines 1105 has been described previously (for example WO2019/099952), such examples retain the original duochrome side-by-side arrangement of image 1100. An example arrangement of duochrome image.

In such previously known duochrome arrangements, the user must individually look at each side of the duochrome image (e.g. image 1100), requiring gaze fixation adjustments, alternate viewing, and memory. Further, focus or accommodation can be activated differentially with either screen, and crucially, no simultaneous red/green central foveal image for detailed comparison is possible. These prior disclosed examples are considered by those skilled in the art as a standard duochrome test, and are considered in the art to be useful for gross evaluation purposes only.

Figure 12B:
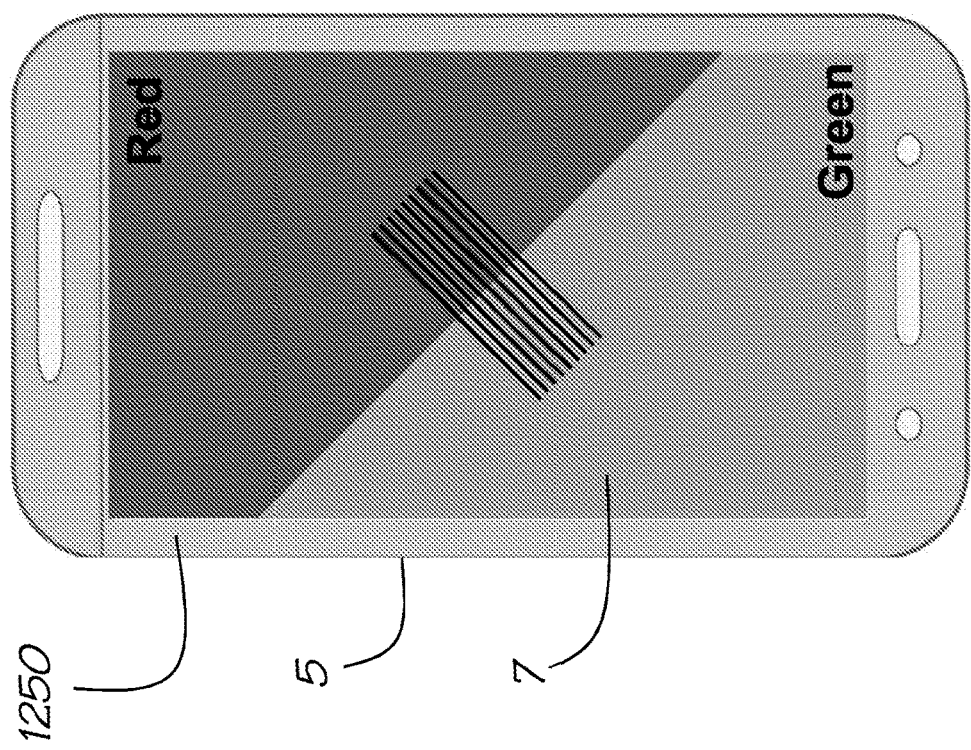
FIG. 12B shows an example arrangement of the SPFF image of FIG. 12A displayed on the screen of a mobile device.
Figure 12A:
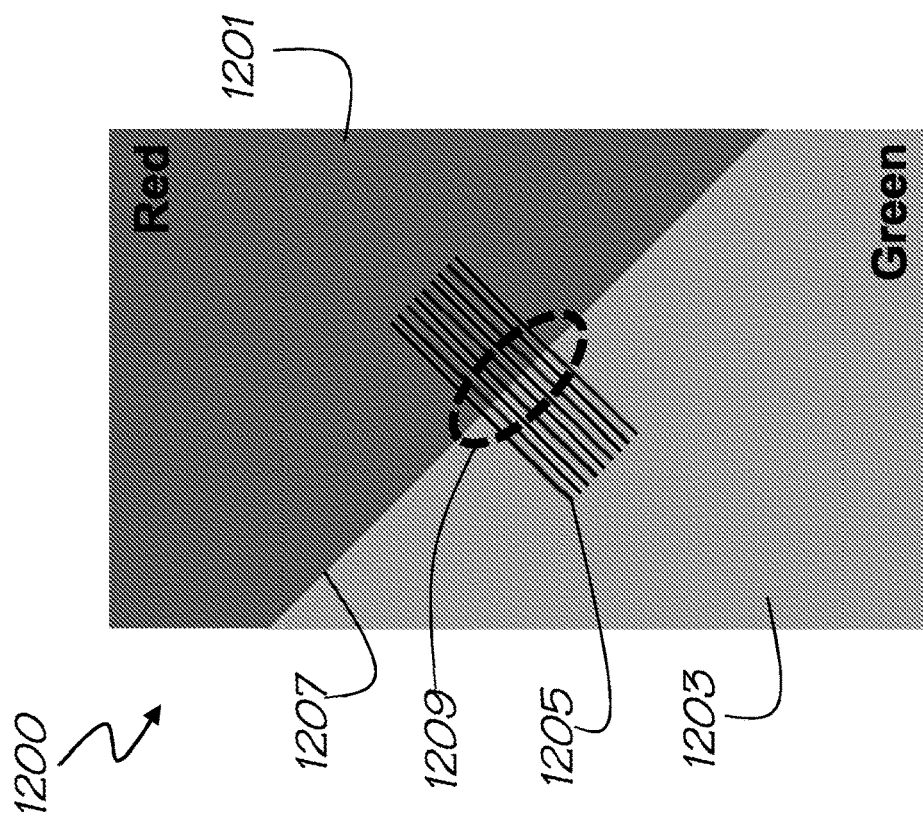
FIG. 12A shows a further arrangement of a SPFF image according to the present disclosure.

The SSPF method described herein and seen in FIGS. 7A to 7C is a significant improvement upon the traditional, side-by-side, duochrome arrangement of FIG. 11. A further example SPFF image 1200 is shown in FIG. 12A and in a particular arrangement of the SPFF image 1200 as shown presented on the display screen 7 of mobile device 5 in FIG. 12B. As in FIGS. 7A to 7C, image 1200 comprises a duochrome background comprising a red background portion 1201 and green background portion 1203 with a hash line image 1205 overlaid across the interface 1207 between the red and green background portions 1201 and 1203. Of critical importance to the design of SSPF is the ability for the image (e.g. the hash line pattern 1205) which is overlaid onto the duochrome background 1201/1203 to be split across the central foveal focus point of the user's eye under test, thus enabling the user to simultaneously fixate on the lines in both portions (i.e. the red 1201 and green 1203 portions of the duochrome image 1200 in about interface region 1209) of the dichromatic presentation. This is made possible by the presentation of lines crossing the red/green interface, and further in the preferred embodiment shown in FIG. 7C where the red/green interface 707 is oriented approximately 90 degrees to the hashed lines 705*c* (See FIG. 7C). FIGS. 7A and 7B in particular show alternate embodiments where the hash line image 705 is angularly offset from the red/green interface 707. In some displays screens 7 of a computing device 5, a non-perpendicular orientation of the hash line image to the red/green interface 707 may experience aliasing of the hash line image 705 at the interface 707 which is not desirable, especially in the case where the user has a high astigmatism magnitude defect in their eye's optics. However, this would be overcome with higher resolution display screens 7 in which case the angle of the image 705 to the interface 707 may be between about 40 degrees to 90 degrees with respect to the interface 707, and preferably at 90° to the interface 707.

In this way, no accommodative differences are possible when evaluating the red/green line clarity, memory effects are eliminated, and no selective preferential viewing phenomenon interferes with the evaluation.

Once the desired Principal Meridian has been located accurately using the SSPF image, the distance from the display screen 7 to the user's eye 3 under test must be determined.

Rather than relying on the more commonly implemented bracketing or thresholding methods to estimate a distance measurement, or the additionally common method of physical measurement using a ruler or tape measure, the systems and methods disclosed herein differ in that it utilises a method reliant upon a live video stream.

Utilising a live video stream enables capability to perform low latency measurements dynamically and in real-time, and gives superior accuracy. This new system is termed herein as Low Latency Dynamic Distance Monitoring (LLDDM).

Modern mobile computing devices typically have frame rates for video capture around 60 frames per second (fps), although newer devices boast rates of up to 960 fps or higher. With high speed video capture rates, comes the ability to enable very low latency distance measurements which is advantageous when attempting to make accurate measurements to within a few millimetres from a device that is being hand held and may be moved slightly (i.e. by natural shake or motion of the user's arm) during the measurement process.

LLDDM enabled high speed measurements further increases the accuracy of the distance determination as multiple measurements may be obtained very quickly and averaged, moded, or other statistical analysis applied to the results.

Once Principal Meridian (1) has been determined, sub-method 210 (astigmatic eye) proceeds by presentation of an image on the display screen 215 comprising a hash line pattern 705B as depicted in FIG. 7B which is oriented orthogonally (90° rotation) to the angle of the radial line selected in step 203. The user is again prompted through instructions 217 on the display screen to carry out the Principal Meridian determination method 400 illustrated in FIG. 4 as discussed below to determine a second Principal Meridian (Meridian 2) to be used in the calculation of the Cylinder component of the eyeglass prescription for the astigmatic eye.

Non-Astigmatic Eye—Method 230

If input received 203 from the user indicates a selected line of the image presented in step 201, then the software application then presents the user with an image on the display screen comprising a hash line pattern 705C as depicted in FIG. 7C which is oriented vertically, in the present arrangement, however, in the case where no astigmatism is present in the user's eye, then the orientation of the hash pattern in the image in sub-method 230 is irrelevant and may equally be oriented horizontally or at any convenient angle in between. As above, the SSPF image of FIG. 7C may be provided with a duochrome background comprising a red background portion and a green (or blue) background portion as a further duochrome test as discussed above.

Since there is no secondary astigmatism axis in this case then the Principal Meridian determination method 400, discussed in detail below, only needs to be performed once.

In alternate arrangements, and primarily for users with a colour vision deficiency, the software application disclosed herein may provide an option for the user to remove the red/green (or blue) background if they desire which may assist the use in identifying the correct distance at which the lines appear clear.

Principal Meridian Determination—Method 400

FIG. 4 illustrates the method 400 for determination of the Principal Meridians which are required for calculation of the eyeglass prescription. Sub-methods 210 and 230 of method 200 shown in FIG. 3 discussed above, both each utilise a Principal Meridian procedure 400 in order to determine the Sphere measurement of the eyeglass prescription—this process is repeated twice in sub-method 210 for the astigmatic eye to determine the refractive component in both the power meridians (the meridian with maximum power and the meridian with minimum power).

Firstly, the software application then presents the user with the SSPF image on the display screen 7 (e.g. step 211 of method 200 above) comprising a hash line pattern as depicted in various embodiments in FIGS. 7A to 7C. The user is then directed 401 through instructions presented on the display screen of mobile device 5 to move the display screen of the mobile device 5 away from the eye until the lines of the image blur and the lines on the red background portion are clearer than the lines on the green background portion. Then the user is prompted 403 to move the phone closer until the line images on the red and green background portions first become equally clear. Once the lines are equally clear, the user provides an input signal to the software via a designated region of touch sensitive display and the LLDDM software proceeds to calculate the Principal Meridian 407 by a measurement of the distance 405 from the display screen to the user's eye. To convert the distance measurement to the Principal Meridian the distance measurement is converted to Diopters, where Diopter is defined as the "inverse of a meter", i.e. 1/m. So, if the measurement is 50 cm, or ½ m, inverting from ½ m gives a Principal Meridian of 2D.

Distance Measurement

To determine the Principal Meridians, the software application must measure or estimate the distance between the image displayed on the visual display screen of mobile device 5 and the user's eye. There are many various methods which may be employed for determining distances using an optical camera such as, for example, a forward-facing camera embedded in a mobile computing device such as a smartphone or tablet device as would readily be appreciated by the skilled addressee. Many such methods for obtaining distance or depth information can be employed using binocular vision with two cameras located side-by side in a similar manner to the way in which the human eyes determine depth information for presentation to the brain. However, the majority of mobile computing devices to date only incorporate a single camera solution, hence alternate methods for obtaining depth information is necessary.

Figure 8:
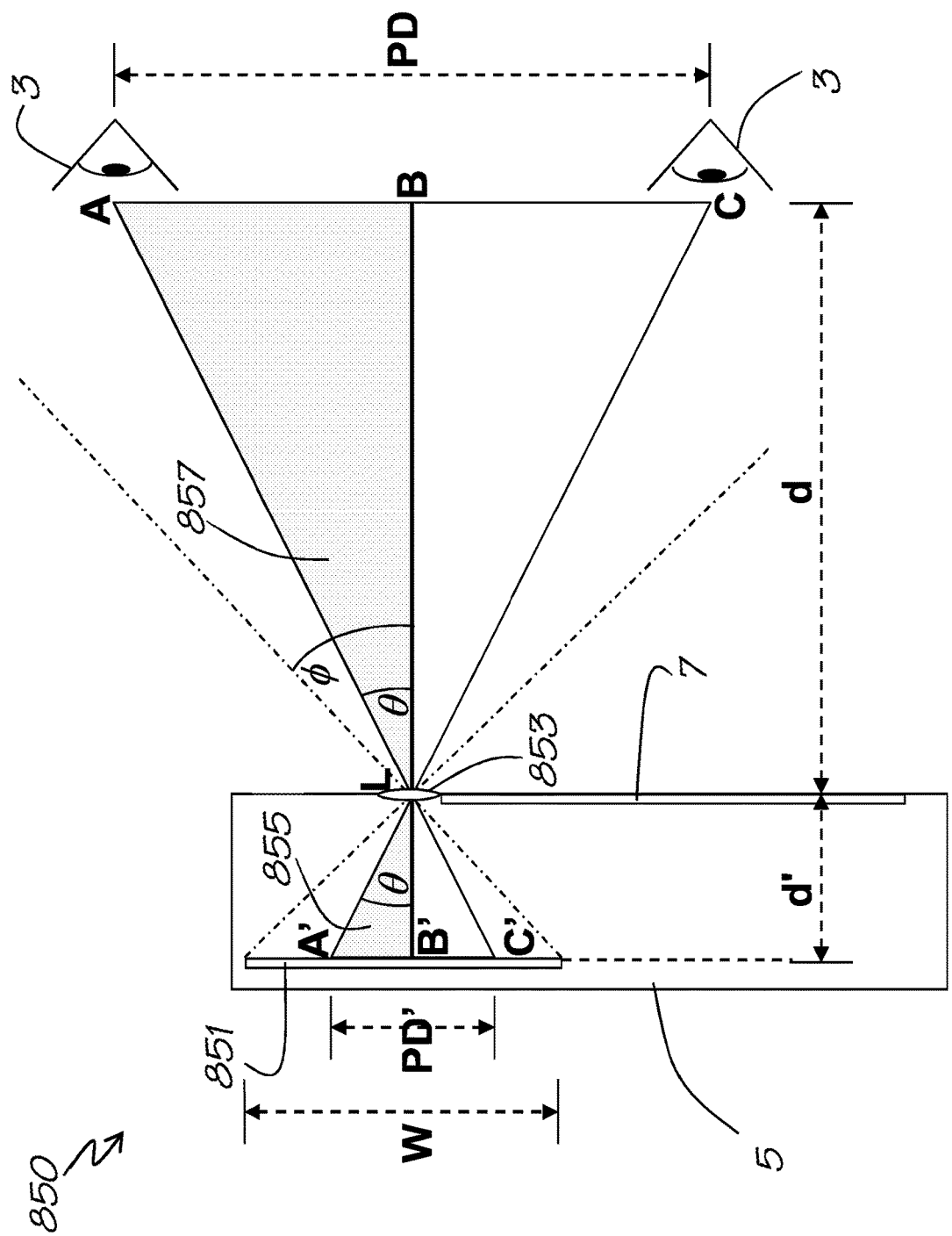
FIG. 8 illustrates schematically a system for obtaining a distance measurement in a single camera arrangement utilising similar triangles to determine the distance, d, from the display screen of a mobile device and the eyes of a user.

FIG. 8 illustrates schematically a system 850 for obtaining a distance measurement in a single camera arrangement utilising similar triangles to determine the distance, d, from the display screen 7 of device 5 and the eyes 3 of user 1. Device 5 comprises a single camera arrangement comprising an image sensor 851 and a focusing lens 853. The triangles 857 and 855 formed between vertices ABL and A'B'L respectively are Similar subtending equal angles θ from the lens 853 (located at vertex L). The distance, d', between lens 853 and the plane of image sensor 851 is known from manufacturer specifications for mobile device 5. The interpupillary distance, PD (line segment AC) is generally consistent within a population so as an initial estimate, this distance PD can be pre-entered into the software application. In further arrangements, the software application may accept user input of their specific interpupillary distance, PD, to provide a more accurate measurement. The PD must be known for the subsequent calculations within about +/−2 mm for the results to be sufficiently accurate (to within 0.5D). Accurate PD consistently gives prescription accuracy within about 0.25D. When determining the Principal Meridians in method 400 (step 405) above, the location of the image of the user's pupils are determined via common image processing and identification methods and the distance between the centroids of the pupils in pixels of the image sensor is translated into an actual distance, PD', in metres using manufacturer specifications of the image sensor used in mobile device 5. Once the pixel distance, PD' (line segment A'C'), is known, then the distance, d, from lens L 855 to the plane AC of the user's eyes 3 is found by comparing segment ratios of similar triangles ABL 857 and A'B'L 855 where:

$$d = d' \frac{PD}{PD'}.$$

Measurement of the distance, d, to within ±5 mm results in an adequate calculation of the user's eyeglass prescription within the 0.25 Diopter steps of available optical power options available for correction optics. The distance measurement accuracy becomes more important with higher powers, i.e. Shorter distances. For example, if D=1/m, if m is sufficiently large then small errors have little impact on the final prescription value, however, if m is small, then small errors can impart significant errors into the reported eyeglass prescription result. Accuracy of the distance d within +/−5 mm gives great results (+/−0.25D) for the range of distances needed to be measured by the software application in operation when testing the acuity of a user. If however, the error in the distance d is within +/−10 mm, then the software application will still provide acceptable results within about +/−0.50D accuracy in the prescription value reported. In the process of method 400, measurement d is then stored in the volatile memory as the Principal Meridian to be used in the calculation of the eyeglass prescription.

In this particular distance measurement arrangement, it is essential that the device 5 is able to discern both pupils of the user's eyes 3 else the imaged distance PD' of the eyes 3 on the image sensor 751 cannot be determined. In particular arrangements, the software application may provide a visual indication on the display 7 to inform the user that both pupils have been detected before the user initiates the measurement to allow the user to adjust the position of the device with respect to their eyes, open their eyes wider, or adjust the lighting as necessary for the software application to be able to make an automatic measurement of the Principal Meridian distance.

In an alternate arrangement, if preferred, the user also has the option of physically measuring the distance from the eye to the display and entering that value into the software application directly. Additionally, if the display needs to be extended further from the eye than the user can reach, then the user can either enlist the help of another person or steady the display and then move away from the display.

In alternate arrangements, the application software may instead estimate the angle 2θ subtended by the user's eyes when imaged on the image sensor 751 in comparison to the angular field of view, 2φ, of the camera lens 753. In this case, the distance, d, from the lens 753 of device camera to the user's eyes 3 is given by:

$$d=PD/[2\tan(\emptyset PD'/2W)].$$

where W is the width of image sensor 751.

In alternate arrangements still, the application software may further comprise means including hardware and/or program instructions for automatic pupillary distance calculations in order to automatic direct measurement of distance between the display screen and the user's eye.

Prescription Calculation

To convert the stored Meridian data to the user's eyeglass prescription, both Principal Meridian distances are converted to powers, in Diopters (D=1/m). The lowest power (least minus power, meridian 1) is reported first as the Sphere value. The higher power (meridian 2) has the lowest power subtracted from it (to give the difference), and the difference is reported as the Cylinder value, then the Axis value is reported from the radial lines as discussed above. For example, Principal Meridian 1 is measured as 50 cm, and meridian 2 at 30 cm. Meridian 1=½ m inverted gives 2D. Principal Meridian 2=⅓ m inverted gives 3D. So, in this example, the eyeglass prescription for that eye of the user is reported as −2.00/−1.00×Axis.

Returning now to FIG. 3 and method 200, once the Principal Meridians have been determined, this is combined with the Clearest Line Meridian stored in volatile memory of device 5 from step 205 and the software application calculates the Sphere, Cylinder and Axis components of that eye's refractive error to provide the user's specific eyeglass prescription for the current eye under test and stores the result in volatile memory of the device 5. The software application checks whether both eyes have been tested. In particular arrangements, the software application may be configured to receive input from the user as to whether testing of their other eye is necessary, and thus may allow the user to only test a single eye in accordance with requirements. If preferred, the user also has the option of physically measuring the distance from the eye to the display, and entering that value. Additionally, if the display needs to be extended further from the eye than the user can reach, then the user can either enlist the help of another person or steady the display and then move away from the display.

Trial Studies

In an initial trial of the software application and eye test systems and methods disclosed herein, the eye test was undertaken by a group of 27 participants who had no understanding of optics or optometry. All subjects underwent, in this order:

Brief history and symptoms probe;
Fundus photography (to rule in-out suitability);
Autorefraction;
Retinoscopy;
Subjective refraction; and
An early prototype of the eye test software application as disclosed herein administered on a mobile computing device.

In the initial stages of the test, none of the subject were removed due to ocular pathology, however one participant was removed due to amblyopia (i.e. lazy eye).

All participants eyeglass prescription as calculated by the eye test software application were within 0.75 dioptres of their prescription as determined by normal subjective refraction (i.e. as compared against the participant's prescribed result as determined by a combination of objective and subjective refraction—that is, the final optometrist's prescription), and 65% of the sphero-cylindrical results reported with the eye test application were within 0.25 dioptres.

65% of sphero-cylindrical results from this trial study obtained by the eye test software application as disclosed herein were comparable to subjective refraction by an experienced optometrist. All eyeglass prescription results from the eye test software application, regardless of pass/fail, would give acceptable and desirable outcomes to the user for myopes who are either uncorrected or significantly under corrected. These Version 1 prototype results outperformed the Shin-Nippon autorefractor.

Figure 10:
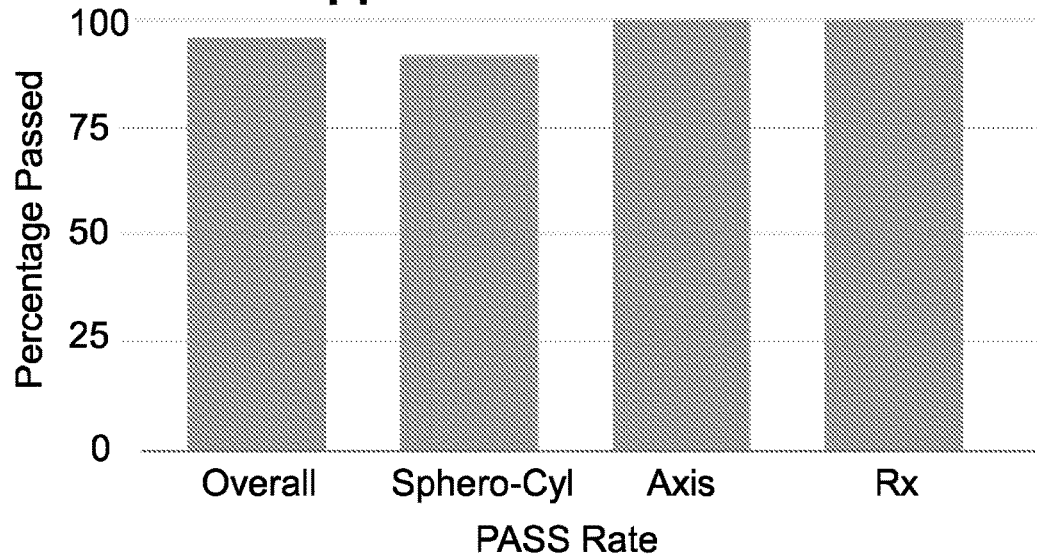
FIG. 10 shows a graph of the result of a trial study comparing the accuracy of the eyeglass prescription calculated using the eye test systems and methods disclosed herein.
Figure 10:
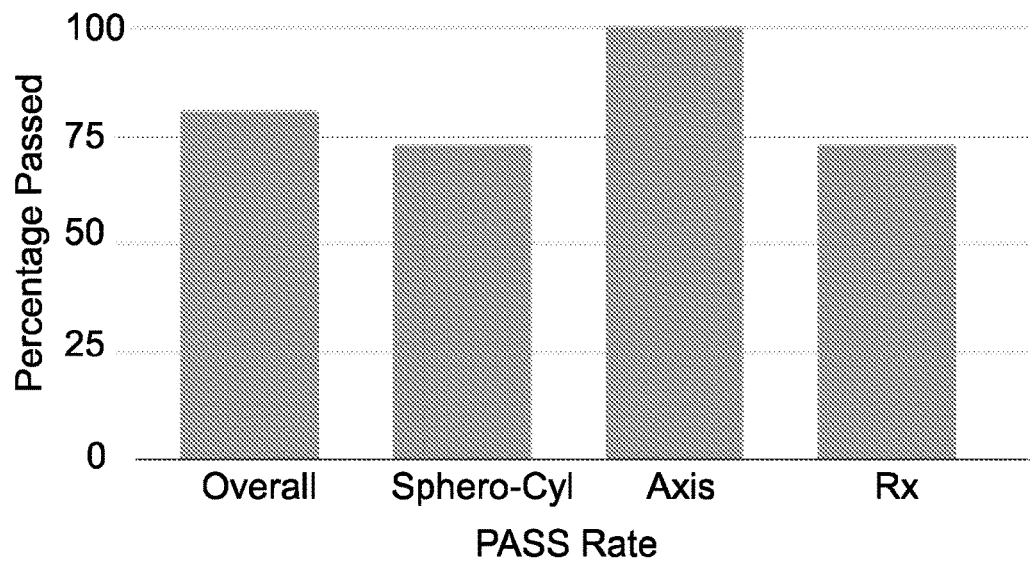

In comparison, the autorefractor device used in the study achieved a sphero-cylindrical pass rate of only 73%. None of the failed results from the auto-refactor would give acceptable and desirable visual correction outcomes for myopes. These results are fairly consistent with what might be expected from autorefraction, thus indicating that the eye test software application as disclosed herein provides a significant improvement in determination of an eyeglass prescription which would result in a favourable visual correction for a user over the likely result obtained from an autorefraction device. FIG. 10 shows a graph of the Pass rate for the eye test software application as disclosed herein compared with the pass rate from the autorefractor results for the trial participants.

Hyperopic Eye Arrangement

As noted above, in the discussion of method 100, if the user 1 is not able to identify any clearer image at step 105, or if the user 1 identifies the image on the green background portion (e.g. background portion 503 of FIG. 5) to be clearer than that on the red background portion (e.g. background portion 501 of FIG. 5) of the duochrome background image, then it is assumed that the user is hyperopic (farsighted) in that particular eye. In this case, the method 100 is halted 150 and the user may be provided with an alternate procedure for determination of their unique eyeglass prescription as noted in step 155 of FIG. 2. In a particular arrangement of a suitable alternate procedure, the user 1 may be offered the option of receiving an optical lens (test lens) of sufficient positive power which they can hold in front of their eye for the duration of the testing procedure of method 200 described above. The power of the additional lens is determined so as to effectively render the user's eye artificially myopic by a known amount, and the test can proceed as usual, with the software application then taking into account the positive lens power of the additional lens when calculating the user's eyeglass prescription. An appropriate test lens can be found by the following procedure: move an image of detail closer until it blurs, i.e. find the closest distance that an object can be seen relatively clearly. Measurement of that distance is obtained. Using the user's age and comparing that to a table of expected accommodative function for age and race, the distance correction can be estimated, and an appropriate positive power lens can be sent to the user 1 such that the methods 100, 200, and 300 described above can be carried out normally.

Alternate Prescription Determination Methods

The methods 100, 200, and 300 and associated sub-methods described above are considered to be the preferred methods for determining the eyeglass prescription for a user utilising a mobile computing device. However, additional methods of obtaining the optical prescription are provided for and may be useful for people who cannot communicate, have difficulty following the instructions provided by the software application, or for a variety of other reasons cannot reliably complete test routine A.

On occasion, an additional lens may be required by the user to obtain the best refractive result as discussed above in relation to an example alternate procedure in the event that at least one of the user's eyes is hyperopic.

In a further arrangement for conducting an eye test for a hyperopic eye, there is provided a further embodiment wherein the user performs the testing procedure whilst facing a mirror, and observing the smartphone's screen virtual image in the mirror. High contrast circular images (black and white) may be useful in determining a suitable eyeglass prescription in a hyperopic eye when viewed virtually (e.g. as a virtual image in a mirror).

Retinoscopic Reflex Alternate Method

In a further arrangement for conducting an eye test, the software application adapted to operate on a mobile computing device 5 may be optionally configured to generate, or instruct the user to generate reflexes from the retina, for example, utilising a flashlight or light incorporated in mobile device 5 which are examined by analysing the images of the user's eye which are captured during the test to determine the user's refractive error, and thus an optical prescription.

In a further arrangement, the camera and flashlight system of mobile device 5 provides a convenient way to illuminate the pupils via way of a retinoscopic reflex. In this particular arrangement, the software application executed by the processor of mobile device 5 utilises the flashlight system to direct bright light into the user's eye through the eye pupil, whereupon the light reflects off the retina and returns out of the eye through the pupil, giving rise to the retinoscopic reflex (often referred to as the red-eye effect in photography). The speed of movement of the retinoscopic reflex with respect to the speed of movement of the light source, and the brightness of the retinoscopic reflex can be examined to determine the eye's refractive error. Whilst it is possible for the user to complete this task independently, it is much easier and much more accurate for the user (the subject) to enlist the help of another person (the operator) to operate the mobile device 5 for this procedure.

In particular for this arrangement, the user firstly completes the lines test as illustrated in FIG. 6A as discussed above to identify the axis of cylinder (Axis), if the user is able to.

The operator assisting the user holds the mobile device vertically about 40 cm-50 cm from the user's eye to be tested. The user is directed to look into the distance, gazing just beside the device 5, and with a relaxed eye posture (which is explained by instructions provided on the display by the software application). The user follows instructions given by the software application and slowly moves the mobile device 5 up/down, left/right, and diagonally in both the approximate 45 degree and 135 degree meridians. The retinoscopic reflex produced is captured by the software application and analysed to produce the user's specific eyeglass prescription for the current eye under test.

Additionally, the retinoscopic reflex may be captured at varying distances from the eye, with only the brightness and appearance of the retinoscopic reflex needing to be examined to determine the user's specific eyeglass prescription for the current eye under test.

If the retinoscopic reflex produced via the mobile device's illumination system is deemed by the system as inadequate (or operator if the operator is sufficiently proficient with the use of the invention), then the invention may be used with the light source being from either an internal or external infrared transmitter, if available. External infrared light sources are readily available in the form of remote control units designed for and supplied with appliances such as television sets, DVD players and the like. The infrared light source is held flat perpendicularly to the mobile device, and the distance from the light source to the camera is measured. The distance measurement is accounted for in the software application.

Following the instructions, the operator follows a procedure similar to that described above, and directs the infrared light beam into the subject's eye whilst the subject attends to a distant point, gazing barely past (almost coincident to) the light source. The retinoscopic reflex produced is captured by the smartphone camera system, and the general reflex, and/or the distinct arcuate pattern produced within these reflexes are evaluated by the invention software to generate the prescription result for Sphere, Cylinder, and Axis.

It may be necessary at times to capture multiple retinoscopic images via either method, or to record continuously the image capture using the smartphones video camera system in order for the invention to gather sufficient data for a reliable optical prescription result. In any case, the user is guided by the invention application.

At all times, the distance from the eye is measured using the phones camera system, but the user may preferably be provided with the option of manual entry if preferred (presumably by an experienced operator), for both the bright light source retinoscopic method, or the infrared photorefraction method.

Presbyopia Evaluation Method

Once the distance prescription is knows or estimated from one or more of the methods disclosed above, a near addition result may be calculated by the software application. Additionally, the user may use the photoretinoscopy or photorefraction functions of the software application to determine the near addition according to typical procedures as would be appreciated by the skilled addressee. The procedure of image capture is essentially the same as for the distance Rx procedure via either photoretinoscopy or photorefraction, however it differs in that the user attends to the plane of the light source/camera during the image capture procedure, with the mobile device 5 being held at the distance from the eye that the subject would like to read, or view a computer monitor, etc. (i.e. the user's desired working distance). Instructions for this near procedure are provided for in the invention, wherein, in particular arrangements, the procedure will be the same as for distance evaluation (i.e. the test procedure discussed above, the difference being that the user looks at the phone screen rather than a distant object. The reflex generation and analysis would be the same, and the result altered by taking into account the distance of the phone from the eye(s).

Ophthalmic Medications Tracking

In further arrangements, the application software may be additionally configured to provide ophthalmic support to the user beyond simple determination of their specific eyeglass prescription. For example, therapy specific tracking functionality has the ability to improve the outcomes for patients undergoing long term eye drop therapy by increasing compliance with the entire treatment regimen over very long timeframes whilst keeping the ECP (or multiple ECPs over time) informed of patient progress as required for timely intervention.

Therapy specific tracking has the significant advantage that it removes the need for unnecessary follow up visits, and associated costs, as the treatment parameters are monitored continuously and trigger follow up visits if and when needed. Therapy specific tracking has the significant advantage that it also ensures timely and appropriate ECP visits, assisting the ECP to deliver time and cost-effective treatment management.

Additionally, the ability for large nationwide therapy programs to be implemented and managed efficiently is possible, with large data collection possible for project and research purposes being collated ongoing and in real time across any and/or all jurisdictions globally.

Atropine Therapy Management

Myopia is an important and widely underestimated public health problem with a looming economic burden. Myopia has been misconstrued to be a benign ocular refractive condition. The economic burden of high myopia pathology will be tremendous, stemming from both direct costs related to surgical treatment; and indirect long-term vision impairment costs. The software applications disclosed herein may be further configured to address the need for governments worldwide to develop and manage public policies and interventions to prevent people from developing high myopia and its associated visual impairment.

Atropine therapy involves using eye drops once per day. It is the most effective myopia control strategy and is realistic and suitable for large population scale programs. Atropine therapy is a long term treatment regimen lasting 10+ years for many people which requires the eye drops be instilled at about the same time each day and has been found to be more effective if first instillation of eye drops is alternated each day. Atropine therapy typically takes around 1 year to become effective.

A user undergoing atropine therapy typically also requires modification of their eyeglass prescription to include reading additions which are sometimes needed in the spectacle prescription after Atropine builds up. Reading additions are also sometimes needed in the spectacle prescription if binocular function is upset, and this additional Reading addition further helps reduce myopic progression. Consequently, the user's spectacle prescriptions should be kept accurate at all times since under-correction has been shown to increase myopia. Thus the systems and methods disclosed herein which enable a user to quickly and accurately obtain an updated prescription without the additional expense and inconvenience of regular repeat visits to their ophthalmic health professional.

Added functionality to the invention via way of an optional Ophthalmic Medications Tracking module assists atropine users and ECPs to successfully manage 1) Atropine Therapy, and 2) Spectacle correction specific to the atropine therapy period.

The Ophthalmic Medication Tracking module is provided with the capability to perform and mange a variety of tasks relevant to the therapeutic regime, including, for example:

Accept a start time/date for atropine therapy initialization.
Prompt the daily instillation of atropine at a specific time.
Verify instillation of atropine, and record the time instilled.
Track and manage multiple users at once over one or more accounts (multiple children may be prescribed therapy concurrently and be oversighted by one or more parents).
Track and manage user(s) atropine supplies.
Prompt the user to re-order atropine before supplies are depleted.
Automatically order atropine at a defined remaining supply level, to ensure ongoing uninterrupted therapy.
Prompt the user to test and record their refraction result regularly and nudge to Eye Care. Practitioner (ECP) involvement may be recommended if the result deviates from their current prescription so as to ensure under correction is avoided.
Prompt the user to measure their near binocular posture; prompt ECP visit if values fall outside parameters set by the Eye Test module (or the user's ECP).
Prompt the user to measure their near accommodative status; prompt ECP visit if values fall outside parameters set by the Eye Test module (or the user's ECP).
Alert ECPs of patients who are returning values outside of the defined limits.
Be adaptable to various concentrations of atropine.
Be adaptable to drugs other than atropine.
Be adaptable to various therapy regimens.
Feedback data collected to ECPs.
Feedback data to research teams and or eye health project teams.

The Ophthalmic Medication Tracking module can be advantageously configured for many therapy types in accordance with requirements, including but not limited to Atropine and glaucoma management, ocular autoimmune disease management, ocular surface management, ocular infectious disease treatments and ocular inflammatory disease management.

Computing Device

Figure 9:
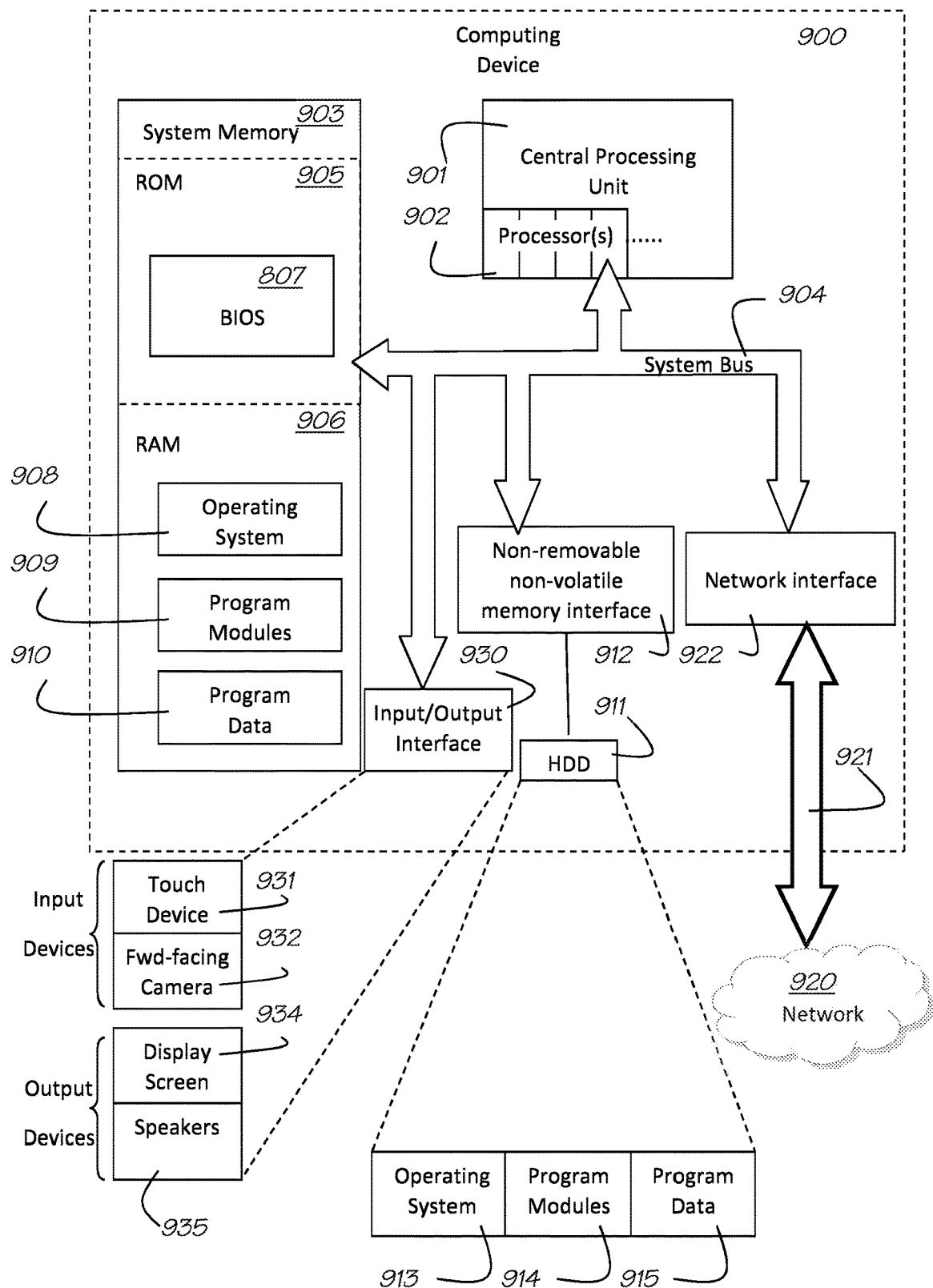
FIG. 9 shows a mobile computing device on which the various embodiments described herein may be implemented in accordance with an embodiment of the present invention.

The methods of providing an eyeglass prescription using a mobile computing device (and associated sub methods (e.g. methods 100, 200, 300 and sub-methods 210 and 230 depicted in FIGS. 1, 2 and 3) may be implemented using a computing device/computer system 900, such as that shown in FIG. 9 wherein the processes of FIGS. 2 to 4 may be implemented as software, such as one or more application programs executable within the computing device 900. In particular, the steps of methods 100, 200, 300 and sub-methods 210 and 230 are effected by instructions in the software that are carried out within the computer system 900. The instructions may be formed as one or more code modules, each for performing one or more particular tasks. The software may also be divided into two separate parts, in which a first part and the corresponding code modules performs the described methods and a second part and the corresponding code modules manage a user interface between the first part and the user. The software may be stored in a computer readable medium, including the storage devices described below, for example. The software is loaded into the computer system 900 from the computer readable medium, and then executed by the computer system 900. A computer readable medium having such software or computer program recorded on it is a computer program product. The use of the computer program product in the computer system 900 preferably effects an advantageous apparatus for providing user accessible eye test applications for mobile devices and in particular to applications for self-determination of eyeglass prescription via mobile computing devices.

In particular arrangements, software modules may be located in a centralised server having processing capabilities e.g. a cloud server arrangement, and which is accessed remotely by the mobile device 5 over a network connection, such as for example a local or wide area Wi-Fi network or via the internet. In a particular arrangement for example. the methods and systems disclosed herein may be accessed by a user via an internet browser page. In this arrangement, the client mobile device 5 receives the image data to be displayed on screen 7 for evaluation of the user's visual status (i.e. the presence or absence of any aberrations in the user's eye affecting their vision) and the refractive errors in the user's eyes, and the client device sends the user's responses to the cloud server for processing to determine the user's eyeglass prescription (which is provided to the user via client mobile device 5). Alternatively, the software modules may be stored on the mobile device 5 in a stand-alone configuration which is not reliant on a network or internet connection since the method steps and processing are all performed locally by the processor(s) of the user's mobile device 5.

With reference to FIG. 9, mobile device 5 is described with reference to an exemplary computing device 900 which is suitable for either stand-alone operation or via a network connection to a remote server. The exemplary computing device 900 can include, but is not limited to, one or more central processing units (CPUs) 901 comprising one or more processors 902, a system memory 903, and a system bus 904 that couples together various system components including the system memory 903 to the processing unit 901. The system bus 904 may be any of several types of bus structures including a memory bus or memory controller, a peripheral bus, and a local bus using any of a variety of bus architectures.

The computing device 900 also typically includes computer readable media, which can include any available media that can be accessed by computing device 900 and includes both volatile and non-volatile media and removable and non-removable media. By way of example, and not limitation, computer readable media may comprise computer storage media and communication media. Computer storage media includes media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computing device 900. Communication media typically embodies computer readable instructions, data structures, program modules or other data in a modulated data signal such as a carrier wave or other transport mechanism and includes any information delivery media. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 903 includes computer storage media in the form of volatile and/or non-volatile memory such as read only memory (ROM) 905 and random-access memory (RAM) 906. A basic input/output system 907 (BIOS), containing the basic routines that help to transfer information between elements within computing device 900, such as during start-up, is typically stored in ROM 905. RAM 906 typically contains data and/or program modules that are immediately accessible to and/or presently being operated on by processing unit 901. By way of example, and not limitation, FIG. 9 illustrates an operating system e08, other program modules e09, and program data 910.

The computing device e00 may also include other removable/non-removable, volatile/non-volatile computer storage media. By way of example only, FIG. 9 illustrates a hard disk drive 911 that reads from or writes to non-removable, non-volatile magnetic media. Other removable/non-removable, volatile/non-volatile computer storage media that can be used with the exemplary computing device include, but are not limited to, magnetic tape cassettes, flash memory cards, digital versatile disks, digital video tape, solid state RAM, solid state ROM, and the like. The hard disk drive 911 is typically connected to the system bus 904 through a non-removable memory interface such as interface 912.

The drives and their associated computer storage media discussed above and illustrated in FIG. 9, provide storage of computer readable instructions, data structures, program modules and other data for the computing device 900. In FIG. 9, for example, hard disk drive 911 is illustrated as storing an operating system 913, other program modules 914, and program data 915. Note that these components can either be the same as or different from operating system 908, other program modules 909 and program data 910. Operating system 913, other program modules 914 and program data 915 are given different numbers hereto illustrate that, at a minimum, they are different copies.

The computing device also includes one or more input/output (I/O) interfaces 930 connected to the system bus e04 including an audio-video interface that couples to output devices including one or more of a display screen 934 and loudspeakers 935. Input/output interface(s) 930 also couple(s) to one or more input devices including, but not limited to, for example a touch sensitive device 931 such as for example a smartphone or tablet device and at least one camera device e.g. a forward-facing camera e32.

Of relevance to the descriptions below, the computing device 900 may operate in a networked environment using logical connections to one or more remote computers. For simplicity of illustration, the computing device e00 is shown in FIG. 9 to be connected to a network 920 that is not limited to any particular network or networking protocols, but which may include, for example Ethernet, Bluetooth or IEEE 802.X wireless protocols. The logical connection depicted in FIG. 9 is a general network connection 921 that can be a local area network (LAN), a wide area network (WAN) or other network, for example, the internet. The computing device 900 is connected to the general network connection e21 through a network interface or adapter 9e which is, in turn, connected to the system bus 904. In a networked environment, program modules depicted relative to the computing device 900, or portions or peripherals thereof, may be stored in the memory of one or more other computing devices that are communicatively coupled to the computing device 900 through the general network connection 921. It will be appreciated that the network connections shown are exemplary and other means of establishing a communications link between computing devices may be used.

Interpretation

Bus

In the context of this document, the term "bus" and its derivatives, while being described in a preferred embodiment as being a communication bus subsystem for interconnecting various devices including by way of parallel connectivity such as Industry Standard Architecture (ISA), conventional Peripheral Component Interconnect (PCI) and the like or serial connectivity such as PCI Express (PCIe), Serial Advanced Technology Attachment (Serial ATA) and the like, should be construed broadly herein as any system for communicating data.

In Accordance With

As described herein, 'in accordance with' may also mean 'as a function of' and is not necessarily limited to the integers specified in relation thereto.

Composite Items

As described herein, 'a computer implemented method' should not necessarily be inferred as being performed by a single computing device such that the steps of the method may be performed by more than one cooperating computing devices.

Similarly objects as used herein such as 'web server', 'server', 'client computing device', 'computer readable medium' and the like should not necessarily be construed as being a single object, and may be implemented as a two or more objects in cooperation, such as, for example, a web server being construed as two or more web servers in a server farm cooperating to achieve a desired goal or a computer readable medium being distributed in a composite manner, such as program code being provided on a compact disk activatable by a license key downloadable from a computer network.

Processes

Unless specifically stated otherwise, as apparent from the following discussions, it is appreciated that throughout the specification discussions utilizing terms such as "processing", "computing", "calculating", "determining", "analysing" or the like, refer to the action and/or processes of a computer or computing system, or similar electronic computing device, that manipulate and/or transform data represented as physical, such as electronic, quantities into other data similarly represented as physical quantities.

Processor

In a similar manner, the term "processor" may refer to any device or portion of a device that processes electronic data, e.g. from registers and/or memory to transform that electronic data into other electronic data that, e.g. may be stored in registers and/or memory. A "computer" or a "computing device" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. The processing system further may include a memory subsystem including main RAM and/or a static RAM, and/or ROM.

Computer-Readable Medium

Furthermore, a computer-readable carrier medium may form, or be included in a computer program product. A computer program product can be stored on a computer usable carrier medium, the computer program product comprising a computer readable program means for causing a processor to perform a method as described herein.

Networked or Multiple Processors

In alternative embodiments, the one or more processors operate as a standalone device or may be connected, e.g. networked to other processor(s), in a networked deployment, the one or more processors may operate in the capacity of a server or a client machine in server-client network environment, or as a peer machine in a peer-to-peer or distributed network environment. The one or more processors may form a web appliance, a network router, switch or bridge, or any machine capable of executing a set of instructions (sequential or otherwise) that specify actions to be taken by that machine.

Note that while some diagram(s) only show(s) a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Additional Embodiments

Thus, one embodiment of each of the methods described herein is in the form of a computer-readable carrier medium carrying a set of instructions, e.g. a computer program that are for execution on one or more processors. Thus, as will be appreciated by those skilled in the art, embodiments of the present invention may be embodied as a method, an apparatus such as a special purpose apparatus, an apparatus such as a data processing system, or a computer-readable carrier medium. The computer-readable carrier medium carries computer readable code including a set of instructions that when executed on one or more processors cause a processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g. a computer program product on a computer-readable storage medium) carrying computer-readable program code embodied in the medium.

Carrier Medium

The software may further be transmitted or received over a network via a network interface device. While the carrier medium is shown in an example embodiment to be a single medium, the term "carrier medium" should be taken to include a single medium or multiple media (e.g. a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media.

Implementation

It will be understood that the steps of methods discussed are performed in one embodiment by an appropriate processor (or processors) of a processing (i.e. computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

Means for Carrying Out a Method or Function

Furthermore, some of the embodiments are described herein as a method or combination of elements of a method that can be implemented by a processor or a processor device, computer system, or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

Connected

Similarly, it is to be noticed that the term connected, when used in the claims, should not be interpreted as being limitative to direct connections only. Thus, the scope of the expression a device A connected to a device B should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other.

Embodiments

Reference throughout this specification to "one embodiment", "an embodiment", "one arrangement" or "an arrangement" means that a particular feature, structure or characteristic described in connection with the embodiment/arrangement is included in at least one embodiment/arrangement of the present invention. Thus, appearances of the phrases "in one embodiment/arrangement" or "in an embodiment/arrangement" in various places throughout this specification are not necessarily all referring to the same embodiment/arrangement, but may. Furthermore, the particular features, structures or characteristics may be combined in any suitable manner, as would be apparent to one of ordinary skill in the art from this disclosure, in one or more embodiments/arrangements.

Similarly it should be appreciated that in the above description of example embodiments/arrangements of the invention, various features of the invention are sometimes grouped together in a single embodiment/arrangement, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment/arrangement. Thus, the claims following the Detailed Description are hereby expressly incorporated into this Detailed Description, with each claim standing on its own as a separate embodiment/arrangement of this invention.

Furthermore, while some embodiments/arrangements described herein include some but not other features included in other embodiments/arrangements, combinations of features of different embodiments/arrangements are meant to be within the scope of the invention, and form different embodiments/arrangements, as would be understood by those in the art. For example, in the following claims, any of the claimed embodiments/arrangements can be used in any combination.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Scope of Invention

Thus, while there has been described what are believed to be the preferred arrangements of the invention, those skilled in the art will recognize that other and further modifications may be made thereto without departing from the spirit of the invention, and it is intended to claim all such changes and modifications as fall within the scope of the invention. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

Industrial Applicability

It is apparent from the above, that the arrangements described are applicable to the mobile device industries, specifically for methods and systems for distributing digital media via mobile devices.

It will be appreciated that the systems and methods described/illustrated above at least substantially provide an eye test application for mobile devices and in particular to applications for self-determination of eyeglass prescription via mobile computing devices.

The systems and methods described herein, and/or shown in the drawings, are presented by way of example only and are not limiting as to the scope of the invention. Unless otherwise specifically stated, individual aspects and components of the systems and methods disclosed herein may be modified, or may have been substituted therefore known equivalents, or as yet unknown substitutes such as may be developed in the future or such as may be found to be acceptable substitutes in the future. The systems and methods disclosed herein may also be modified for a variety of applications while remaining within the scope and spirit of the claimed invention, since the range of potential applications is great, and since it is intended that the present systems and methods be adaptable to many such variations.

The invention claimed is:

1. A system comprising Simultaneous Split Point Focus (SSPF) and Low Latency Dynamic Distance Monitoring (LLDDM) for enabling self determination of eyeglass prescription for a user via a mobile computing device, the device comprising:

volatile and non volatile memory for storing data;
a processor configured for executing program instructions stored in the non volatile memory;
a visual display screen adapted to receive image information from the processor to present instructions and images to a user; and
a camera configured to receive images of the user's pupils during a test situation;
wherein the system comprises application program instructions for directing the processor to undertake a method for determining an eyeglass prescription, the method comprising:
determining if an eye of the user is myopic, and if the user's eye is myopic;
determining Principal and Axis Meridians of a user's eyes while the user is observing the image information on the display screen;
enabling the system of LLDDM for real time determination of the refractive power errors in the Principal and Axis Meridians of a user's eyes in while the user is observing the SSPF image information on the display screen;
calculating Sphere, Cylinder and Axis prescriptions from the Principal and Axis Meridian values obtained via the LLDDM system; and
displaying the calculated prescription values to the user.

2. A system as claimed in claim 1, wherein determining if an eye of the user is myopic comprises a method implemented by execution of program instructions in the processor, the method comprising:
displaying an image on the display screen comprising a first portion having a duochrome background;
providing instructions to the user; and
receiving input from the user with respect to a portion of the image which appears subjectively clearer to the user.

3. A system as claimed in claim 1, wherein determining the Axis Meridian comprises a method implemented by execution of program instructions in the processor, the method comprising:
displaying a radially oriented image on the display screen;
providing instructions to the user; and
receiving input from the user with respect to a portion of the radially oriented image which appears subjectively clearer to the user.

4. A system as claimed in claim 1, wherein determining the Principal Meridians comprises a method implemented by execution of program instructions in the processor, the method comprising:
displaying a hash line image on the display screen comprising a duochrome background and receiving input from the user with respect to a location spaced from the users eye under test where the lines appears subjectively equally clear to the user; and
determining the distance from the display screen to the user's eye under test.

5. A system as claimed in claim 4, wherein the line images displayed on the screen are configured to have a width between about 2 and 8 pixels.

6. A system as claimed in claim 5, wherein the line images displayed on the screen are configured to have a width between about 4 and 8 pixels.

7. A system as claimed in claim 6, wherein the length of the lines displayed on the screen are between about 40 and 60 mm long.

8. A system as claimed in claim 1 comprising a duochrome image comprising:
a duochrome background image with at least two portions separated by an interface; and
an image overlaid on the duochrome background across the interface between the duochrome background portions;
wherein each the image in each of the duochrome background portions is simultaneously imaged to an ocular foveal point of the user's eye under test.

9. A system as claimed in claim 1, wherein the distance from the display screen to the user's eye under test is determined from a live video stream of the user's eyes during a test.

10. A method for self determination of eyeglass prescription for a user via a mobile computing device, the method comprising:
providing a mobile computing device comprising:
a processor configured for executing program instructions stored in the non volatile memory;
a visual display screen adapted to receive image information from the processor to present instructions and images to a user; and
a camera configured to receive images of the user's pupils during a test situation;
wherein the method comprises providing application program instructions for directing the processor to undertake a method for determining an eyeglass prescription, the program instructions comprising:
program code for determining if an eye of the user is myopic, and if the user's eye is myopic;
program code for determining Principal and Axis Meridians of a user's eyes while the user is observing the image information on the display screen; and
program code for calculating Sphere, Cylinder and Axis prescriptions from the Principal and Axis Meridians;
wherein the method further comprises presentation of a duochrome image on the display screen, the duochrome image comprising:
a duochrome background with at least two portions separated by an interface and an image overlaid on the duochrome background across the interface between the duochrome background portions; and
wherein the image in each of the duochrome background portions is simultaneously imaged to an ocular foveal point of the user's eye under test.

11. A method as claimed in claim 10 wherein determining if an eye of the user is myopic comprises program code for displaying an image on the display screen comprising:
a duochrome background;
program code for providing instructions to the user; and
program code for receiving input from the user with respect to a portion of the image which appears subjectively clearer to the user.

12. A method as claimed in claim 10, wherein determining the Axis Meridian comprises: program code for displaying a radially oriented image on the display screen; program code for providing instructions to the user; and program code for receiving input from the user with respect to a portion of the radially oriented image which appears subjectively clearer to the user.

13. A method as claimed in claim 10, wherein determining the Principal Meridians comprises:
program code for displaying a hash line image on the display screen comprising a duochrome background and receiving input from the user with respect to a location spaced from the users eye under test where the lines appears subjectively equally clear to the user; and determining the distance from the display screen to the user's eye under test.

14. A method as claimed in claim 10, wherein the distance from the display screen to the user's eye under test is determined from a live video stream of the user's eyes during a test.

15. A method as claimed in claim 10, wherein the duochrome background comprises a background image having a first portion and a second portion and an interface, wherein the first and second portions are adjacent each other.

16. A method as claimed in claim 15, wherein the first portion comprises a red background portion and the second portion comprises a green or blue background.

17. A method as claimed in claim 15, wherein the hash line image is overlaid over both the red and green background portions and is aligned between about 40 degrees to 90 degrees to the interface.

18. A method as claimed in claim 17, wherein the hash line image is aligned approximately perpendicularly to the interface.

* * * * *